(12) United States Patent
Baxter et al.

(10) Patent No.: US 7,786,116 B2
(45) Date of Patent: Aug. 31, 2010

(54) 2-AMINO-QUINOLINE DERIVATIVES USEFUL AS INHIBITORS OF β-SECRETASE (BACE)

(75) Inventors: Ellen Baxter, Glenside, PA (US); Christopher J. Creighton, San Diego, CA (US); Chih Yung Ho, Lansdale, PA (US); Yifang Huang, Lansdale, PA (US); Tianbao Lu, Churchville, PA (US); Chi Luo, New Hope, PA (US); Allen B. Reitz, Lansdale, PA (US); Charles H. Reynolds, Lansdale, PA (US); Tina Morgan Ross, Royerford, PA (US); Ellen Sieber-McMaster, Langhorne, PA (US)

(73) Assignee: Janssen Pharmaceutica N.V., Beerse (BE)

(*) Notice: Subject to any disclaimer, the term of this patent is extended or adjusted under 35 U.S.C. 154(b) by 0 days.

(21) Appl. No.: 12/362,020

(22) Filed: Jan. 29, 2009

(65) Prior Publication Data

US 2009/0227581 A1  Sep. 10, 2009

Related U.S. Application Data

(60) Provisional application No. 61/024,244, filed on Jan. 29, 2008.

(51) Int. Cl.
| A61K 31/5377 | (2006.01) |
| A61K 31/4709 | (2006.01) |
| C07D 413/14 | (2006.01) |
| C07D 215/38 | (2006.01) |

(52) U.S. Cl. .................... 514/235.2; 514/313; 544/128; 546/159

(58) Field of Classification Search ............... 514/235.2, 514/313; 544/128; 546/159, 160
See application file for complete search history.

(56) References Cited

U.S. PATENT DOCUMENTS

| 4,001,237 A | 1/1977 | Partyka et al. |
| 4,675,047 A | 6/1987 | Serban et al. |
| 4,739,056 A | 4/1988 | Venuti et al. |
| 4,761,416 A | 8/1988 | Fried et al. |
| 5,387,742 A | 2/1995 | Cordell |
| 5,580,003 A | 12/1996 | Malone et al. |
| 5,612,486 A | 3/1997 | McConlogue et al. |
| 5,672,805 A | 9/1997 | Neve |
| 5,720,936 A | 2/1998 | Wadsworth et al. |
| 5,811,633 A | 9/1998 | Wadsworth et al. |
| 5,850,003 A | 12/1998 | McLonlogue et al. |
| 5,877,015 A | 3/1999 | Hardy et al. |
| 5,877,399 A | 3/1999 | Hsiao et al. |
| 6,037,521 A | 3/2000 | Sato et al. |
| 6,071,903 A | 6/2000 | Albright et al. |
| 6,184,435 B1 | 2/2001 | Geen et al. |
| 6,187,922 B1 | 4/2001 | Singh et al. |
| 6,211,428 B1 | 1/2002 | Snow |
| 6,340,783 B1 | 1/2002 | Snow |
| 7,531,545 B2 | 5/2009 | Baxter et al. |
| 2004/0087548 A1 | 5/2004 | Salvati et al. |
| 2004/0209905 A1 | 10/2004 | Kubo et al. |
| 2005/0171111 A1 | 8/2005 | Angibaud et al. |
| 2006/0074105 A1 | 4/2006 | Ware et al. |
| 2006/0079686 A1 | 4/2006 | Baxter et al. |
| 2006/0079687 A1 | 4/2006 | Baxter et al. |
| 2006/0178383 A1 | 8/2006 | Bischoff et al. |
| 2007/0232642 A1 | 10/2007 | Baxter et al. |
| 2008/0194624 A1* | 8/2008 | Baxter et al. ............... 514/313 |
| 2009/0227627 A1 | 9/2009 | Baxter et al. |

FOREIGN PATENT DOCUMENTS

| EP | 406958 | 1/1991 |
| EP | 1407774 | 4/2004 |
| JP | 63-196573 | 8/1988 |
| JP | 04 011255 | 1/1992 |
| WO | 01/38315 | 5/2000 |
| WO | 02/100399 | 12/2002 |
| WO | 2004/022523 | 3/2004 |
| WO | 2004/058686 | 7/2004 |
| WO | 2005/049585 | 6/2005 |
| WO | 2006/017836 | 2/2006 |
| WO | 2006/017844 | 2/2006 |
| WO | 2006/024932 | 3/2006 |
| WO | 2006/078577 | 7/2006 |
| WO | 2007/050612 | 5/2007 |
| WO | 2007/092846 | 8/2007 |
| WO | 2007/092854 | 8/2007 |

OTHER PUBLICATIONS

Citron, Trends in Pharm. Sci., vol. 25, Issue 2, Feb. 2004, 92-97.

(Continued)

Primary Examiner—Kamal A Saeed
Assistant Examiner—Kristin Bianchi
(74) Attorney, Agent, or Firm—Hal Brent Woodrow

(57) ABSTRACT

The present invention is directed to novel 2-amino-quinoline derivatives, pharmaceutical compositions containing them and their use in the treatment of Alzheimer's disease (AD), mild cognitive impairment, senility and/or dementia. The compounds of the present invention are inhibitors of β-secretase, also known as β-site amyloid cleaving enzyme, BACE, BACE1, Asp2, or memapsin2.

11 Claims, No Drawings

OTHER PUBLICATIONS

Cole, et al., Molecular Neurodegeneration 2007, 2:22.
Hamaguchi, et al., Cell. Mol. Life Sci. 63 (2006) 1538-1552.
Database Caplus "Online!" Chemical Abstracts Service, Columbus, Ohio, US. Ishikawa, Fumyoshi et al.: "Quinazolineacetic acid derivatives as platelet aggregation inhibitors". XP00236713.
El Mouedden, M. et al., (Johnson & Johnson Pharmaceutical Research and Development, Division of Janssen Pharmaceutica N.V., Turnhoutseweg 30, Beerse, Belg.), Development of a specific ELISA for the quantitative study of amino-terminally truncated beta-amyloid peptides,. Journal of Neuroscience Methods (2005), 145(1-2), pp. 97-105.
Ermolieff et al., Biochemistry, (2000) vol. 39, p. 12450.
Games, D. et al., (Athena Neurosciences, Inc., South San Francisco, CA, USA), Alzheimer-type neuropathology in transgenic mice overexpressing V717F β-amyloid precursor protein, Nature (London) (1995), 373(6514), pp. 523-527 (V717F mice).
Hsiao, K. et al., (Dep. Neurology, Univ. Minnesota, Minneapolis, MN, USA), Correlative memory deficits, Aβ elevation, and amyloid plaques in transgenic mice, Science (Washington, D. C.) (1996), 274(5284), pp. 99-102 (Tg2576 mice).
Kienzle, F. et. al., Chemical Abstract, 1983, vol. 98, Abstract No. 143363, (or CAPLUS Accession No. 1983:143363).
Kienzle, F., et al. "1,5-Dihydroimdazoquinazoliones as Blood Platelet Aggregation Inhibitors", European Journal of Medicinal Chemistry, 17(6), 547-556.
Larner, A.J.: "Secretases as Therapeutic Targets in Alzheimer's Disease: Patents 2000 2004". Expert Opinion On Therapeutic Patents, Ashley Publications, GB, vol. 14, No. 10, 2004, pp. 1403-1420, XP002404250.
Lewczuk, P. et al., (Department of Psychiatry and Psychotherapy, Molecular Neurobiology Lab, University of Erlangen-Nuremberg, Erlangen, Germany), Neurochemical diagnosis of Alzheimer's dementia by CSF Aβ42, Aβ42/Aβ40 ratio and total tau, Neurobiology of Aging (2004), 25(3), pp. 273-281.
Lins, H. et al., (Department of Neurology, Otto-von-Guericke-University, Magdeburg, Germany), Immunoreactivities of amyloid β peptide(1-42) and total τ C protein in lumbar cerebrospinal fluid of patients with normal pressure hydrocephalus, Journal of Neural Transmission (2004), 111(3), pp. 273-280.
Neve, R. L. et al., (Dep. Genetics, Harvard Medical School and McLean Hospital, Belmont, MA, USA), Transgenic mice expressing APP-C100 in the brain, Neurobiology of Aging (1996), 17(2), pp. 191-203 (APP-C100 mice).
Oddo, S. et al, (Department of Neurobiology and Behavior, University of California, Irvine, Irvine, CA, USA), Triple-transgenic model of Alzheimer's disease with plaques and tangles: Intracellular Aβ and synaptic dysfunction, Neuron (2003), 39(3), pp. 409-421 (APP Triple Transgenic Mice).
Olsson, A. et al., (Sahlgrenska University Hospital, Experimental Neuroscience Section, Institute of Clinical Neuroscience, Goteborg University, Moelndal, Sweden), Measurement of α- and β-secretase cleaved amyloid precursor protein in cerebrospinal fluid from Alzheimer patients, Experimental Neurology (2003), 183(1), pp. 74-80.
Ruberti et al., (Neuroscience Program, International School for Advanced Studies (SISSA), Trieste, Italy), Phenotypic knockout of nerve growth factor in adult transgenic mice reveals severe deficits in basal forebrain cholinergic neurons, cell death in the spleen, and skeletal muscle dystrophy, Journal of Neuroscience (2000), 20(7), pp. 2589-2601 (AD11 mice).
Schoonenboom, N.S. et al., Amyloid β 38, 40, and 42 species in cerebrospinal fluid: More of the same?, Annals of Neurology (2005), 58(1), pp. 139-142.
Sirinathsinghji, D. J. S. (Merck Sharp and Dohme Research Laboratories, Neuroscience Research Centre, Essex, UK.), Transgenic mouse models of Alzheimer's disease, Biochemical Society Transactions (1998), 26(3), pp. 504-508.
Van Leuven, F. (Experimental Genetics Group, Center for Human Genetics, Flemish Institute for Biotechnology (VIB), K.U.Leuven, Louvain, Belg.), Single and multiple transgenic mice as models for Alzheimer's disease, Progress in Neurobiology (Oxford) (2000), 61(3), pp. 305-312.
Vanderstichele, H. et al., (Innogenetics NV, Ghent, Belg.), Standardization of measurement of β-amyloid(1-42) in cerebrospinal fluid and plasma, Amyloid (2000), 7(4), pp. 245-258.
Venuti, M., et al. Inhibitors of Cyclic AMP Phosphodiestrase 2 Structural Variations of N-Cyclohexyl-N-Methyl-4-(1,2,3,5-Tetrahydro-2-Oxoimidazo 2,1-B Quinazo-7-yl-Oxybutyramids J. Medicinal Chemistry, American Chemical Society, vol. 30, No. 2, 1987, pp. 303-318.
Wahlund, L.-O et al., (Karolinska Institute, Section of Geriatric Medicine, Department of Clinical Neuroscience and Family Medicine, Huddinge University Hospital, Stockholm, Sweden), Cerebrospinal fluid biomarkers for disease stage and intensity in cognitively impaired patients, Neuroscience Letters (2003), 339(2), pp. 99-102.
Webb, T. Improved Synthesis of Symmetrical and Unsymmetrical 5,11- Methandibenzo'b.f.1,5-iazocines. Readily Available Inanoscale Structural Units, Journal of Organic Chemistry, vol. 55, No. 1, 1990, pp. 363-365.
Office Action mailed Jun. 19, 2009 in U.S. Appl. No. 11/671,681.
Office Action mailed Sep. 29, 2009 in U.S. Appl. No. 11/671,681.
Office Action mailed Jun. 19, 2008 in U.S. Appl. No. 11/671,703.
Office Action mailed Aug. 20, 2008 in U.S. Appl. No. 11/671,703.
Office Action mailed Feb. 12, 2009 in U.S. Appl. No. 11/671,703.
Office Action mailed Jun. 9, 2009 in U.S. Appl. No. 11/671,703.
Notice of Allowance mailed Nov. 19, 2009 in U.S. Appl. No. 11/671,703.
Office Action mailed Mar. 24, 2009 in U.S. Appl. No. 11/671,732.
Notice of Allowance mailed Sep. 25, 2009 in U.S. Appl. No. 11/671,732.
Notice of Allowance mailed Jan. 6, 2010 in U.S. Appl. No. 11/671,732.
Office Action mailed Aug. 21, 2008 in U.S. Appl. No. 11/197,669.
Office Action mailed Apr. 29, 2009 in U.S. Appl. No. 11/197,669.
Notice of Allowance mailed Dec. 8, 2009 in U.S. Appl. No. 11/197,669.
Office Action mailed May 30, 2008 in U.S. Appl. No. 11/197,608.
Office Action mailed Aug. 20, 2008 in U.S. Appl. No. 11/197,608.
Office Action mailed Apr. 30, 2009 in U.S. Appl. No. 11/197,608.
Notice of Allowance mailed Dec. 8, 2009 in U.S. Appl. No. 11/197,608.
Office Action mailed May 29, 2008 in U.S. Appl. No. 11/197,615.
Office Action mailed Jan. 27, 2009 in U.S. Appl. No. 11/197,615.

* cited by examiner

2-AMINO-QUINOLINE DERIVATIVES USEFUL AS INHIBITORS OF β-SECRETASE (BACE)

CROSS REFERENCE TO RELATED APPLICATIONS

This application claims the benefit of U.S. Provisional Application 61/024,244 filed on Jan. 29, 2008, which is incorporated by reference herein in its entirety.

FIELD OF THE INVENTION

The present invention is directed to novel 2-amino-quinoline derivatives, pharmaceutical compositions containing them and their use in the treatment of Alzheimer's disease (AD), mild cognitive impairment, senility and/or dementia. The compounds of the present invention are inhibitors of β-secretase, also known as β-site amyloid cleaving enzyme, BACE, BACE1, Asp2, or memapsin 2.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibillary tangles which are generated by hyperphosphorylation of tau protein and amyloid plaques which form by aggregation of β-amyloid$_{1-42}$ (Aβ$_{1-42}$) peptide. Aβ$_{1-42}$ forms oligomers and then fibrils, and ultimately amyloid plaques. The oligomers and fibrils are believed to be especially neurotoxic and may cause most of the neurological damage associated with AD. Agents that prevent the formation of Aβ$_{1-42}$ have the potential to be disease-modifying agents for the treatment of AD. Aβ$_{1-42}$ is generated from the amyloid precursor protein (APP), comprised of 770 amino acids. The N-terminus of Aβ$_{1-42}$ is cleaved by β-secretase (BACE), and then γ-secretase cleaves the C-terminal end. In addition to Aβ$_{1-42}$, γ-secretase also liberates Aβ$_{1-40}$ which is the predominant cleavage product as well as Aβ$_{1-38}$ and Aβ$_{1-43}$. These Aβ forms can also aggregate to form oligomers and fibrils. Thus, inhibitors of BACE would be expected to prevent the formation of Aβ$_{1-42}$ as well as Aβ$_{1-40}$, Aβ$_{1-38}$ and Aβ$_{1-43}$ and would be potential therapeutic agents in the treatment of AD.

SUMMARY OF THE INVENTION

The present invention is directed to compounds of formula (I)

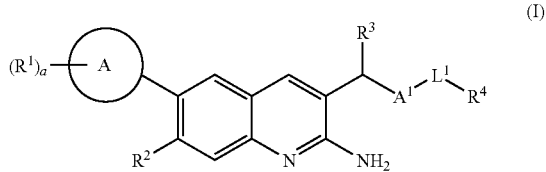

wherein
a is an integer from 0 to 4;
R$^1$ is selected from the group consisting of halogen, C$_{1-4}$alkyl, C$_{1-4}$alkoxy, halogenated C$_{1-4}$alkyl and halogenated C$_{1-4}$alkoxy;

is selected from the group consisting of aryl and heteroaryl;
R$^2$ is selected from the group consisting of hydrogen and C$_{1-4}$alkoxy;
R$^3$ is selected from the group consisting of hydrogen, C$_{1-8}$alkyl, hydroxy substituted C$_{2-8}$alkyl, NR$^A$R$^B$ substituted C$_{2-8}$alkyl, —C$_{1-4}$alkyl-O—C$_{1-4}$alkyl, cycloalkyl, —(C$_{1-4}$alkyl)-cycloalkyl, heterocycloalkyl and —(C$_{1-4}$alkyl)-heterocycloalkyl; wherein R$^A$ and R$^B$ are each independently selected from the group consisting of hydrogen and C$_{1-4}$alkyl;
A$^1$ is selected from the group consisting of —(CH$_2$)$_b$—; wherein b is an integer from 2 to 4;
L$^1$ is selected from the group consisting of —NR$^C$— and —C(O)—NR$^C$—; wherein R$^C$ is selected from the group consisting of hydrogen, C$_{1-8}$alkyl, hydroxy substituted C$_{1-4}$alkyl, —C$_{1-4}$alkyl-O—C$_{1-4}$alkyl and C$_{5-7}$cycloalkyl;
R$^4$ is selected from the group consisting of C$_{1-8}$alkyl, C$_{2-12}$alkenyl, —C$_{1-4}$alkyl-O—C$_{1-4}$alkyl, —C$_{1-4}$alkyl-NR$^D$R$^E$, —C$_{1-4}$alkyl-OH, cycloalkyl, —C$_{1-4}$alkyl-cycloalkyl, partially unsaturated carbocyclyl, —C$_{1-4}$alkyl-(partially unsaturated carbocyclyl), aryl, aralkyl, heteroaryl, —C$_{1-4}$alkyl-heteroaryl, heterocycloalkyl and —C$_{1-4}$alkyl-heterocycloalkyl;
wherein R$^D$ and R$^E$ are each independently selected from the group consisting of hydrogen and C$_{1-4}$alkyl;
and wherein the cycloalkyl, partially unsaturated carbocyclyl, aryl, heteroaryl or heterocycloalkyl, whether alone or as part of a substituent group, is optionally substituted with one or more substituents independently selected from the group consisting of fluoro, C$_{1-4}$alkyl, —C$_{1-4}$alkyl-O—C$_{1-4}$alkyl, carboxy, —C(O)O—C$_{1-4}$alkyl and aralkyl;
alternatively, L$^1$ is —NR$^C$— and R$^C$ and R$^4$ are taken together with the nitrogen atom to which they are attached to form a ring structure selected from the group consisting of 1-pyrazolyl, 1-imidazolyl and 1-(1,2,3-triazolyl); wherein the 1-pyrazolyl, 1-imidazolyl or 1-(1,2,3-triazolyl) is optionally substituted with a substituent selected from the group consisting of C$_{1-6}$alkyl;
and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the β-secretase enzyme, comprising administering to a subject in need thereof a therapeutically effective amount of any of the compounds or pharmaceutical compositions described above.

Further exemplifying the invention are methods of inhibiting the β-secretase enzyme, comprising administering to a subject in need thereof a therapeutically effective amount of any of the compounds or pharmaceutical compositions described above.

An example of the invention is a method of treating a disorder selected from the group consisting of Alzheimer's disease (AD), mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of any of the compounds or pharmaceutical compositions described above.

Another example of the invention is the use of any of the compounds described above in the preparation of a medicament for treating: (a) Alzheimer's Disease (AD), (b) mild cognitive impairment, (c) senility, (d) dementia, (e) dementia with Lewy bodies, (f) Down's syndrome, (g) dementia associated with stroke, (h) dementia associated with Parkinson's disease and (i) dementia associated with beta-amyloid, in a subject in need thereof.

DETAILED DESCRIPTION OF THE INVENTION

The present invention is directed to compounds of formula (I)

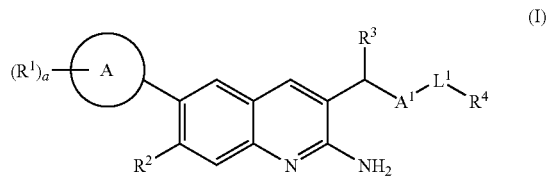

(I)

wherein a, $R^1$,

$R^2$, $R^3$, $A^1$, $L^1$ and $R^4$ are as herein defined, and pharmaceutically acceptable salts thereof. The compounds of formula (I) are inhibitors of the β-secretase enzyme (also known as β-site cleaving enzyme, BACE, BACE1, Asp2 or memapsin 2), and are useful in the treatment of Alzheimer's disease (AD), mild cognitive impairment (MCI), senility, dementia, dementia associated with stroke, dementia with Lewy bodies, Down's syndrome, dementia associated with Parkinson's disease and dementia associated with beta-amyloid, preferably Alzheimer's disease, mild cognitive impairment or dementia, more preferably Alzheimer's disease.

In an embodiment of the present invention, a is an integer from 0 to 3. In another embodiment of the present invention, a is an integer from 0 to 2. In another embodiment of the present invention, a is an integer from 1 to 2. In another embodiment of the present invention, a is 1.

In an embodiment of the present invention, $R^1$ is selected from the group consisting of halogen, $C_{1-4}$alkoxy, halogenated $C_{1-4}$alkyl and halogenated $C_{1-4}$alkoxy. In another embodiment of the present invention, $R^1$ is selected from the group consisting of halogen, $C_{1-2}$alkoxy, fluorinated $C_{1-2}$alkyl and fluorinated $C_{1-2}$alkoxy.

In another embodiment of the present invention, $R^1$ is selected from the group consisting of fluoro, methoxy, ethoxy, trifluoromethyl and trifluoromethoxy. In another embodiment of the present invention, $R^1$ is selected from the group consisting of fluoro, methoxy and ethoxy. In another embodiment of the present invention, $R^1$ is selected from the group consisting of fluoro and ethoxy. In another embodiment of the present invention, $R^1$ is selected from the group consisting of fluoro, methoxy and trifluoromethoxy.

In an embodiment of the present invention,

is selected from the group consisting of aryl and heteroaryl. In another embodiment of the present invention,

is selected from the group consisting of phenyl, 2-thienyl, 2-pyrrolyl, 2-pyridyl and 7-indolyl. In another embodiment of the present invention,

is selected from the group consisting of phenyl and 2-thienyl. In another embodiment of the present invention,

is selected from the group consisting of phenyl, 2-thienyl and 7-indolyl. In another embodiment of the present invention,

is selected from the group consisting of phenyl and 7-indolyl.

In an embodiment of the present invention, $R^2$ is selected from the group consisting of hydrogen and $C_{1-4}$alkoxy. In another embodiment of the present invention, $R^2$ is selected from the group consisting of hydrogen and $C_{1-2}$alkoxy. In another embodiment of the present invention, $R^2$ is selected from the group consisting of hydrogen, methoxy and ethoxy. In another embodiment of the present invention, $R^2$ is hydrogen. In another embodiment of the present invention, $R^2$ is selected from the group consisting of hydrogen and ethoxy.

In an embodiment of the present invention, $R^3$ is selected from the group consisting of $C_{1-8}$alkyl, hydroxy substituted $C_{2-8}$alkyl, $NR^A R^B$ substituted $C_{2-8}$alkyl, cycloalkyl, —($C_{1-4}$ alkyl)-cycloalkyl, heterocycloalkyl and —($C_{1-4}$alkyl)-heterocycloalkyl; wherein $R^A$ and $R^B$ are each independently selected from the group consisting of hydrogen and $C_{1-4}$alkyl. In another embodiment of the present invention, $R^3$ is selected from the group consisting of cycloalkyl and heterocycloalkyl. In another embodiment of the present invention, $R^3$ is selected from the group consisting of (S)-cyclohexyl and 4-tetrahydropyranyl. In another embodiment of the present invention, $R^3$ is 4-tetrahydropyranyl.

In an embodiment of the present invention, $A^1$ is selected from the group consisting of —$(CH_2)_b$—; wherein b is an integer from 2 to 4. In another embodiment of the present invention, $A^1$ is selected from the group consisting of —$(CH_2)_b$; wherein b is an integer from 2 to 3. In another embodiment of the present invention, $A^1$ is selected from the group consisting of —$CH_2CH_2$— and —$CH_2CH_2CH_2$—. In another embodiment of the present invention, $A^1$ is —$CH_2CH_2$—.

In an embodiment of the present invention, $L^1$ is selected from the group consisting of —$NR^C$— and —$C(O)$—$NR^C$—. In another embodiment of the present invention, $L^1$ is —$C(O)$—$NR^C$—.

In an embodiment of the present invention, $R^C$ is selected from the group consisting of hydrogen, $C_{1-8}$alkyl, hydroxy substituted $C_{1-4}$alkyl and $C_{5-7}$cycloalkyl. In another embodiment of the present invention, $R^C$ is selected from the group consisting of hydrogen, $C_{1-8}$alkyl and cycloalkyl. In another embodiment of the present invention, $R^C$ is selected from the group consisting of hydrogen, methyl, 3,3-dimethyl-n-butyl and cyclohexyl. In another embodiment of the present invention, $R^C$ is selected from the group consisting of hydrogen, 3,3-dimethyl-n-butyl and cyclohexyl. In another embodiment of the present invention, $R^C$ is selected from the group consisting of hydrogen, methyl and 3,3-dimethyl-n-butyl.

In an embodiment of the present invention, $R^4$ is selected from the group consisting of $C_{1-8}$alkyl, —$C_{1-4}$alkyl-O—$C_{1-4}$alkyl, —$C_{1-4}$alkyl-$NR^D R^E$, —$C_{1-4}$alkyl-OH, cycloalkyl, —$C_{1-4}$alkyl-cycloalkyl, aryl, aralkyl, heteroaryl, —$C_{1-4}$alkyl-heteroaryl, heterocycloalkyl and —$C_{1-4}$alkyl-heterocycloalkyl; wherein the cycloalkyl, partially unsaturated carbocyclyl, aryl, heteroaryl or heterocycloalkyl, whether alone or as part of a substituent group, is optionally substituted with one or more substituents independently selected from the group consisting of fluoro, $C_{1-4}$alkyl, carboxy, —C(O)O—$C_{1-4}$alkyl and aralkyl; and wherein $R^D$ and $R^E$ are each independently selected from the group consisting of hydrogen and $C_{1-4}$alkyl. In another embodiment of the present invention, $R^4$ is selected from the group consisting of $C_{1-8}$alkyl, hydroxy substituted $C_{1-6}$alkyl, —$C_{1-4}$alkyl-O—$C_{1-4}$alkyl-, cycloalkyl, —$C_{1-2}$alkyl-cycloalkyl, aralkyl, heteroaryl, —$C_{1-2}$alkyl-heteroaryl and —$C_{1-2}$alkyl-heterocycloalkyl; wherein the cycloalkyl, aryl, heteroaryl or heterocycloalkyl, whether alone or as part of a substituted group is optionally substituted with $C_{1-4}$alkyl.

In another embodiment of the present invention, $R^4$ is selected from the group consisting of 1-(3,3,-dimethyl-n-butyl), 1-hydroxy-ethyl, 1-(2,2-dimethyl-3-hydroxy-n-propyl), t-butoxy-ethyl, cyclohexyl, 1-adamantyl, cyclopropyl-methyl-, cyclohexyl-methyl-, benzyl, 2-(1-methyl-imidazolyl), 2-pyridyl-methyl-, 1-pyrrolidinyl-ethyl-, 5-thiazolyl-methyl- and 4-morpholinyl-ethyl-. In another embodiment of the present invention, $R^4$ is selected from the group consisting of 1-(3,3-dimethyl-n-butyl), t-butoxy-ethyl, 1-adamantyl, cyclohexyl-methyl-, benzyl, 2-(1-methyl-imidazolyl), 2-pyridyl-methyl-, 1-pyrrolidinyl-ethyl-, 5-thiazolyl-methyl- and 4-morpholinyl-ethyl-. In another embodiment of the present invention, $R^4$ is selected from the group consisting of 1-(3,3-dimethyl-n-butyl), cyclohexyl-methyl-, benzyl, 2-(1-methyl-imidazolyl), 2-pyridyl-methyl-, 1-pyrrolidinyl-ethyl-, 5-thiazolyl-methyl- and 4-morpholinyl-ethyl-. In another embodiment of the present invention, $R^4$ is selected from the group consisting of 1-(3,3,-dimethyl-n-butyl), 1-adamantyl, cyclohexyl-methyl-, 2-(1-methyl-imidazolyl), 5-thiazolyl-methyl- and 4-morpholinyl-ethyl-.

In an embodiment of the present invention, $L^1$ is —$NR^C$— and $R^C$ and $R^4$ are taken together with the nitrogen atom to which they are attached to form a ring structure selected from the group consisting of 1-pyrazolyl, 1-imidazolyl and 1-(1,2,3-triazolyl); wherein the 1-pyrazolyl, 1-imidazolyl or 1-(1,2,3-triazolyl) is optionally substituted with a substituent selected from the group consisting of $C_{1-6}$alkyl. In another embodiment of the present invention, $L^1$ is —$NR^C$— and $R^C$ and $R^4$ are taken together with the nitrogen atom to which they are bound to form 1-(1,2,3-triazolyl); wherein the 1,2,3-triazolyl is optionally substituted with a $C_{1-4}$alkyl. In another embodiment of the present invention, $L^1$ is —$NR^C$— and $R^C$ and $R^4$ are taken together with the nitrogen atom to which they are bound to form 1-(4-t-butyl-1,2,3-triazolyl).

Additional embodiments of the present invention, include those wherein the substituents selected for one or more of the variables defined herein (i.e. a, $R^1$, (A)

$R^2$, $R^3$, $A^1$, $L^1$ and $R^4$) are independently selected to be any individual substituent or any subset of substituents selected from the complete list as defined herein. In another embodiment of the present invention is any single compound or subset of compounds selected from the representative compounds listed in Tables 1-2 below.

Representative compounds of the present invention are as listed in Table 1 to 2 below. Unless otherwise noted, wherein a stereogenic center is present in the listed compound, the compound was prepared as a mixture of stereo-configurations. Where a stereogenic center is present, the (S)- and (R)-designations are intended to indicate that the exact stereo-configuration of the center has not been determined.

TABLE 1

Representative Compounds of Formula (I)

| ID No. | (R¹)ₐ A | R² | R³ | b | L¹ | R⁴ |
|---|---|---|---|---|---|---|
| 1 | 2-fluoro-phenyl | H | 4-tetrahydro-pyranyl | 2 | —C(O)—NH— | hydroxy-ethyl- |
| 2 | 2-fluoro-phenyl | H | 4-tetrahydro-pyranyl | 2 | —C(O)—NH— | cyclopropyl-methyl- |
| 3 | 2-fluoro-phenyl | H | 4-tetrahydro-pyranyl | 3 | —N(CH₃)— | cyclopropyl-methyl- |
| 4 | 2-fluoro-phenyl | H | 4-tetrahydro-pyranyl | 2 | —C(O)—N(CH₃)— | cyclopropyl-methyl- |
| 5 | 2-fluoro-phenyl | H | 4-tetrahydro-pyranyl | 3 | —NH— | 1-(3,3-dimethyl-n-butyl) |
| 6 | 2-fluoro-phenyl | H | 4-tetrahydro-pyranyl | 3 | —NH— | 1-(2,2-dimethyl-3-hydroxy-n-propyl) |
| 7 | 2-fluoro-phenyl | H | 4-tetrahdyro-pyranyl | 2 | —C(O)—NH— | 1-(3,3-dimethyl-n-butyl) |
| 8 | 2-fluoro-phenyl | H | 4-tetrahydro-pyranyl | 3 | —N(CH₃)— | 1-(3,3-dimethyl-n-butyl) |
| 9 | 2-fluoro-phenyl | H | 4-tetrahydro-pyranyl | 2 | —C(O)—NH— | 1-(2,2-dimethyl-3-hydroxy-n-propyl) |
| 10 | 2-fluoro-phenyl | H | 4-tetrahydro-pyranyl | 3 | —NH— | t-butoxy-ethyl- |
| 11 | 2-fluoro phenyl | H | (S)-cyclohexyl | 2 | —C(O)—N(CH₃)— | cyclohexyl |
| 12 | 2-fluoro-phenyl | H | 4-tetrahydro-pyranyl | 2 | —C(O)—NH— | cyclohexyl-methyl- |
| 13 | 2-fluoro-phenyl | H | 4-tetrahydro-pyranyl | 3 | —N(CH₃)— | cyclohexyl-methyl- |
| 14 | 2-fluoro-phenyl | H | 4-tetrahydro-pyranyl | 2 | —C(O)—N(CH₃)— | 1-(3,3-dimethyl-n-butyl) |
| 15 | 2-fluoro-phenyl | H | 4-tetrahydro-pyranyl | 2 | —C(O)—NH— | t-butoxy-ethyl- |
| 16 | 2-fluoro-phenyl | —OCH₃ | 4-tetrahydro-pyranyl | 3 | —NH— | 1-(3,3-dimethyl-n-butyl) |
| 18 | 2-fluoro-phenyl | H | 4-tetrahydro-pyranyl | 2 | —C(O)—N(CH₃)— | cyclohexyl-methyl- |
| 19 | 2-fluoro-phenyl | —OCH₃ | 4-tetrahydro-pyranyl | 2 | —C(O)—NH— | 1-(3,3-dimethyl-n-butyl) |
| 21 | 2-thienyl | H | 4-tetrahydro-pyranyl | 2 | —C(O)—NH— | 1-adamantyl |
| 23 | 2-fluoro-phenyl | H | 4-tetrahydro-pyranyl | 2 | —C(O)—NH— | 1-adamantyl |
| 24 | 2-pyrrolyl | H | 4-tetrahydro-pyranyl | 2 | —C(O)—N(CH₂CH₂—C(CH₃)₃)— | 2-(1-methyl-imidazolyl) |
| 25 | phenyl | H | 4-tetrahydro-pyranyl | 2 | —C(O)—N(CH₂CH₂—C(CH₃)₃)— | 2-(1-methyl-imidazolyl) |
| 26 | 2-fluoro-phenyl | H | 4-tetrahydro-pyranyl | 3 | —N(CH₂CH₂—C(CH₃)₃)— | benzyl |
| 27 | 2-pyridyl | H | 4-tetrahydro-pyranyl | 2 | —C(O)—N(CH₂CH₂—C(CH₃)₃)— | 2-(1-methyl-imidazolyl) |
| 28 | 2-fluoro-phenyl | H | 4-tetrahydro-pyranyl | 3 | —N(CH₂CH₂—C(CH₃)₃)— | 2-pyridyl-methyl- |
| 29 | 2-fluoro-phenyl | H | 4-tetrahydro-pyranyl | 3 | —N(CH₂CH₂—C(CH₃)₃)— | 2-(1-methyl-imidazolyl) |

TABLE 1-continued

Representative Compounds of Formula (I)

| ID No. | A (R¹)ₐ | R² | R³ | b | L¹ | R⁴ |
|---|---|---|---|---|---|---|
| 30 | 2-fluoro-phenyl | H | 4-tetrahydro-pyranyl | 3 | —N(cyclohexyl)— | 1-pyrrolidinyl-ethyl |
| 31 | 2-thienyl | H | 4-tetrahydro-pyranyl | 2 | —C(O)—N(CH₂CH₂—C(CH₃)₃)— | 2-(1-methyl-imidazolyl) |
| 33 | 2-fluoro-phenyl | H | 4-tetrahydro-pyranyl | 3 | —N(CH₂CH₂—C(CH₃)₃)— | 5-thiazolyl methyl- |
| 34 | 2-fluoro-phenyl | H | 4-tetrahydro-pyranyl | 2 | —C(O)—N(CH₂CH₂—C(CH₃)₃)— | benzyl |
| 35 | 2-fluoro-phenyl | H | 4-tetrahydro-pyranyl | 2 | —C(O)—N(CH₂CH₂—C(CH₃)₃)— | 2-pyridyl-methyl |
| 36 | 2-methoxy-phenyl | H | 4-tetrahydro-pyranyl | 3 | —N(CH₂CH₂—C(CH₃)₃)— | 2-(1-methyl-imidazolyl) |
| 37 | 4-fluoro-phenyl | H | 4-tetrahydro-pyranyl | 2 | —C(O)—N(CH₂CH₂—C(CH₃)₃)— | 2-(1-methyl-imidazolyl) |
| 38 | 3-fluoro-phenyl | H | 4-tetrahydro-pyranyl | 2 | —C(O)—N(CH₂CH₂—C(CH₃)₃)— | 2-(1-methyl-imidazolyl) |
| 39 | 2-fluoro-phenyl | H | 4-tetrahydro-pyranyl | 2 | —C(O)—N(CH₂CH₂—C(CH₃)₃)— | 2-(1-methyl-imidazolyl) |
| 41 | 2-fluoro-phenyl | H | 4-tetrahydro-pyranyl | 2 | —C(O)—N(cyclohexyl) | 1-pyrrolidinyl-ethyl- |
| 42 | 2-fluoro-phenyl | H | 4-tetrahydro-pyranyl | 2 | —C(O)—N(CH₂CH₂—C(CH₃)₃)— | 5-thiazolyl methyl- |
| 43 | 2-fluoro-phenyl | H | 4-tetrahydro-pyranyl | 3 | —N(CH₂CH₂—C(CH₃)₃)— | 4-morpholinyl-ethyl- |
| 45 | 2-methoxy-phenyl | H | 4-tetrahydro-pyranyl | 2 | —C(O)—N(CH₂CH₂—C(CH₃)₃)— | 2-(1-methyl-imidazolyl) |
| 46 | 2,4-phenyl | H | 4-tetrahydro-pyranyl | 2 | —C(O)—N(CH₂CH₂—C(CH₃)₃)— | 2-(1-methyl-imidazolyl) |
| 47 | 2-fluoro-phenyl | H | 4-tetrahydro-pyranyl | 2 | —C(O)—N(CH₂CH₂—C(CH₃)₃)— | 4-morpholinyl-ethyl- |
| 49 | 7-indolyl | H | 4-tetrahydro-pyranyl | 2 | —C(O)—N(CH₂CH₂—C(CH₃)₃)— | 2-(1-methyl-imidazolyl) |
| 50 | 4-ethoxy-phenyl | H | 4-tetrahydro-pyranyl | 2 | —C(O)—N(CH₂CH₂—C(CH₃)₃)— | 2-(1-methyl-imidazolyl) |
| 51 | 2-ethoxy-phenyl | H | 4-tetrahydro-pyranyl | 2 | —C(O)—N(CH₂CH₂—C(CH₃)₃)— | 2-(1-methyl-imidazolyl) |
| 52 | 2-fluoro-phenyl | —OCH₃ | 4-tetrahydro-pyranyl | 3 | —N(cyclohexyl)— | 4-morpholinyl-ethyl- |
| 53 | 2-fluoro-phenyl | —OCH₃ | 4-tetrahydro-pyranyl | 2 | —C(O)—N(cyclohexyl)— | 4-morpholinyl-ethyl- |
| 54 | 3-trifluoro-methyl-phenyl | H | 4-tetrahydro-pyranyl | 2 | —C(O)—N(CH₂CH₂—C(CH₃)₃)— | 2-(1-methyl-imidazolyl) |
| 55 | 2-trifluoro-methyl-phenyl | H | 4-tetrahydro-pyranyl | 2 | —C(O)—N(CH₂CH₂—C(CH₃)₃)— | 2-(1-methyl-imidazolyl) |
| 56 | 2-trifluoro-methoxy-phenyl | H | 4-tetrahydro-pyranyl | 2 | —C(O)—N(CH₂CH₂—C(CH₃)₃)— | 2-(1-methyl-imidazolyl) |

TABLE 2

Representative Compounds of Formula (I)

| ID No. | $(R^1)_a$ — A | $R^2$ | $R^3$ | $A^1$ | $-L^1-R^4$ is $-NR^C-R^4$ where $R^C$ and $R^4$ are taken together |
|---|---|---|---|---|---|
| 17 | 2-fluoro-phenyl | $-OCH_3$ | 4-tetrahydro-pyranyl | $-CH_2CH_2-$ | 1-(4-t-butyl-1,2,3-triazolyl) |
| 20 | 2-methoxy-phenyl | $-OCH_3$ | 4-tetrahydro-pyranyl | $-CH_2CH_2-$ | 1-(4-t-butyl-1,2,3-triazolyl) |
| 22 | 2-fluoro-phenyl | $-OCH_2-CH_3$ | 4-tetrahydro-pyranyl | $-CH_2CH_2-$ | 1-(4-t-butyl-1,2,3-triazolyl) |

As used herein, unless otherwise noted, the term "halogen" shall mean chlorine, bromine, fluorine and iodine. Preferably, the halogen is fluoro or chloro. More preferably, the halogen is fluoro.

As used herein, unless otherwise noted, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, n-pentyl, isopentyl, hexyl, heptyl, octyl, nonyl, decyl, and the like. Similarly, the term "$C_{1-8}$alkyl" shall include straight and branched chains comprising one to eight carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to $-CF_3$, $-CH_2-CF_3$, $-CF_2-CF_2-CF_2-CF_3$, and the like. Similarly, the term "fluorinated $C_{1-4}$alkyl" shall mean any $C_{1-4}$alkyl group as defined above substituted with at least one fluoro atom. Suitable examples include but are not limited to $-CF_3$, $-CH_2-CF_3$, $-CF_2-CF_2-CF_2-CF_3$, and the like.

As used herein, unless otherwise noted, the term "hydroxy substituted $C_{1-4}$alkyl" shall mean a straight or branched chain $C_{1-4}$alkyl, wherein the $C_{1-4}$alkyl is substituted with one or more, preferably one to three hydroxy groups, more preferably one to two hydroxy groups. Most preferably, the $C_{1-4}$alkyl group is substituted with one hydroxy group. Preferably, wherein the $C_{1-4}$alkyl group has a terminal carbon atom, the hydroxy group is bound at said terminal carbon atom.

As used herein, unless otherwise noted, the term "alkenyl" whether used alone or as part of a substituent group, shall include straight and branched chains containing at least one, preferably one to three, more preferably one to two, unsaturated double bonds. For example, alkenyl radicals include $-CH=CH_2$, 2-propenyl, 3-butenyl, 2-butenyl, 3,7-dimethyl-octa-2,6-dienyl, and the like. Similarly, the term "$C_{2-8}$alkenyl" shall include straight and branched alkenyl chains comprising two to eight carbon atoms.

As used herein, unless otherwise noted, the term "alkynyl" whether used alone or as part of a substituent group, shall include straight and branched chains containing at least one, preferably one to three, more preferably one to two, most preferably one, unsaturated triple bonds. For example, alkynyl radicals include $-CCH$ (i.e. ethynyl), 2-propynyl, 3-butynyl, and the like. Similarly, the term "$C_{2-8}$alkynyl" shall include straight and branched alkynyl chains comprising two to eight carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include but are not limited to $-OCF_3$, $-OCH_2-CF_3$, $-OCF_2-CF_2-CF_2-CF_3$, and the like. Similarly, the term "fluorinated $C_{1-4}$alkoxy" shall mean any $C_{1-4}$alkoxy group as defined above substituted with at least one fluoro atom. Suitable examples include but are not limited to $-OCF_3$, $-OCH_2-CF_3$, $-OCF_2-CF_2-CF_2-CF_3$, and the like.

As used herein, unless otherwise noted, "aryl" shall refer to fully conjugated aromatic ring structures such as phenyl, naphthyl, and the like.

As used herein, unless otherwise noted, the term "cycloalkyl" shall mean any stable monocyclic, bicyclic, polycyclic, bridged or spiro-bound, saturated ring system. Suitable examples include, but are not limited to, cyclopropyl, cyclobutyl, cyclopentyl, cyclohexyl, cycloheptyl, cyclooctyl, norboranyl, adamantyl, spiropentane, 2,2,2-bicyclooctyl, and the like. Further, the term "$C_{5-7}$cycloalkyl" shall mean a cycloalkyl as herein defined containing 5 to 7 carbon atoms. Unless otherwise noted, "cycloalkyl" groups do not contain N, O or S heteroatoms.

As used herein, unless otherwise noted, the term "partially unsaturated carbocyclyl" shall mean any stable monocyclic, bicyclic, polycyclic, bridge or spiro-bound ring system containing at least one carbon atom which is not part of an unsaturated bond (i.e. a double or triple bond) or any bicyclic, polycyclic, bridged or spiro-bound, partially aromatic (e.g. benzo-fused) rings system. Suitable examples include, but are not limited to 1,2,3,4-tetrahydro-naphthyl, fluorenyl, 9,10-dihydroanthracenyl, indanyl, and the like. Unless otherwise noted, "partially unsaturated carbocyclyl" groups do not contain N, O or S heteroatoms.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, 5-tetrazolyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic (e.g. benzo-fused) bicyclic ring system containing at least one heteroatom selected from the group consisting of O, N and S, optionally containing one to four additional heteroatoms independently selected from the group consisting of O, N and S; or a 7-16 membered saturated, partially unsaturated or partially aromatic polycyclic or bridged ring system containing at least one heteroatom selected from the group consisting of O, N and S, optionally containing one or four additional heteroatoms indepdently selected from O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, tetrahydropyranyl, azepinyl, 2,3-dihydro-1,4-benzodioxanyl, 1-aza-bicyclo[2.2.2]octanyl, 3-quinuclidinyl, and the like.

As used herein, the notation "*" shall denote the presence of a stereogenic center.

When a particular group is "substituted" (e.g., cycloalkyl, aryl, heterocycloalkyl, heteroaryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl-($C_1$-$C_6$alkyl)-aminocarbonyl-($C_1$-$C_6$alkyl)-" substituent refers to a group of the formula

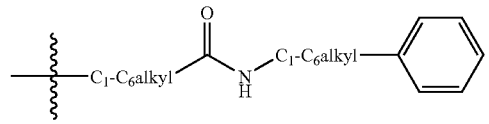

Unless otherwise noted, the position at which substituent groups on the compounds of formula (I) are bound to the 2-amino-quinoline core shall be denoted as follows:

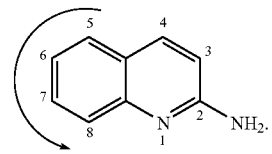

One skilled in the art will recognize that some substituent groups are bivalent (i.e. bound through two points of attachment), for example the substituent groups of $A^1$ and $L^1$ in the compounds of formula (I) and formula (II) as described herein. One skilled in the art will further recognize that the bivalency of these groups is defined by the two bond indicators—i.e. dashes—in the listing of said groups. For example, in the definition of $A^1$, the group —$C_{1-4}$-alkyl- is intended to mean an alkyl chain comprising one to four carbon atoms, wherein the chain is bivalent. Similarly, the $A^1$ group —$CH_2$-cyclopropyl- is intended that the -cyclopropyl- group is bivalent and therefore bound into the molecule such that one carbon atom is bound to the —$CH_2$— group of $A^1$ and at another carbon atom is bound to the rest of the molecule as defined herein.

Abbreviations used in the specification, particularly the Schemes and Examples, are as follows:

| | |
|---|---|
| Ac = | Acetyl (i.e. —C(O)—$CH_3$) |
| AD = | Alzheimer's Disease |
| APP = | Amyloid Precursor Protein |
| BACE = | Beta Amyloid Site Cleaving Enzyme |
| $BH_3$•THF = | Borane Tetrahydrofuran Complex |
| DCM = | Dichloromethane |
| DIPEA or DIEA = | Diisopropylethylamine |
| DMAP = | 4-N,N-Dimethylaminopyridine |
| DMF = | N,N-Dimethylformamide |
| DMSO = | Dimethylsulfoxide |
| EDC or EDCI = | 1-(3-Dimethylaminopropyl)-3-ethylcarbodiimide hydrochoride |
| $Et_2O$ = | Diethyl Ether |
| EtOAc = | Ethyl acetate |
| EtOH = | Ethanol |
| HBTU = | O-Benzotriazol-1-yl-N, N, N', N'-tetramethyluronium hexafluorophosphate |
| HOBT or 1-HOBt = | 1-Hydroxybenzotriazole |
| HPLC = | High Pressure Liquid Chromatography |
| LC/MS = | Liquid Chromatography/Mass Spectrometry |
| LHMDS = | Lithium hexamethylisilazide |
| MCI = | Mild Cognitive Impairment |
| MeOH = | Methanol |
| $NH_4OAc$ = | Ammonium Acetate |
| NMR = | Nuclear Magnetic Resonance |
| Pd(PPh$_3$)$_4$ = | Tetrakis(triphenylphosphine) palladium |
| OM99-2 = | 4-amino-4-{1-[2-carbamoyl-1-(4-{1-[3-carboxy-1-(1-carboxy-2-phenyl-ethylcarbamoyl)- |

| | -continued |
|---|---|
| | propylcarbamoyl]-ethylcarbamoyl}-2-hydroxy-1-isobutyl-pentylcarbamoyl)-ethylcarbamoyl]-2-methyl-propylcarbamoyl}-butyric acid |
| t-BuOH = | tert-butanol (HO—C(CH$_3$)$_3$) |
| TEA = | Triethylamine |
| TFA = | Trifluoroacetic Acid |
| THF = | Tetrahydrofuran |

As used herein, unless otherwise noted, the term "isolated form" shall mean that the compound is present in a form which is separate from any solid mixture with another compound(s), solvent system or biological environment. In an embodiment of the present invention, the compound of formula (I) is present as an isolated form.

As used herein, unless otherwise noted, the term "substantially pure compound" shall mean that the mole percent of impurities in the isolated base is less than about 5 mole percent, preferably less than about 2 mole percent, more preferably, less than about 0.5 mole percent, most preferably, less than about 0.1 mole percent. In an embodiment of the present invention, the compound of formula (I) is substantially pure.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is substantially free of corresponding salt forms.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid. Representative bases which may be used in the preparation of pharmaceutically acceptable salts include, but are not limited to, the following: ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example benzyl, tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1999.

As used herein, unless otherwise noted, the term "oxygen protecting group" shall mean a group which may be attached to an oxygen atom to protect said oxygen atom from participating in a reaction and which may be readily removed following the reaction. Suitable examples include, but are not limited to methyl, benzyl, trimethylsilyl, tert-butyldimethylsilyl, acetate, 1-ethoxyethyl, and the like. Other suitable nitrogen protecting groups may be found in texts such as T. W. Greene & P. G. M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems.

One skilled in the art will recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

Where the processes for the preparation of the compounds according to the invention give rise to mixture of stereoisomers, these isomers may be separated by conventional techniques such as preparative chromatography or recrystallization. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1999. The protecting groups may be removed at a convenient subsequent stage using methods known from the art.

Compounds of formula (I) wherein $L^1$ is —C(O)—$NR^C$— may be prepared according to the process outlined in Scheme 1.

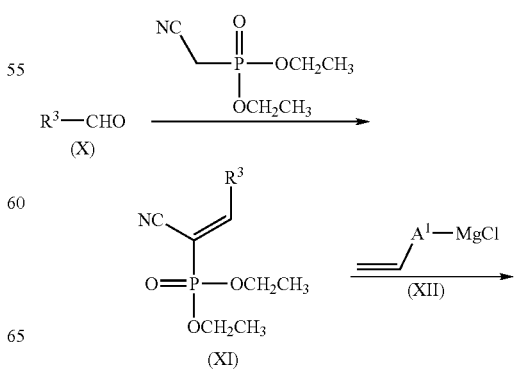

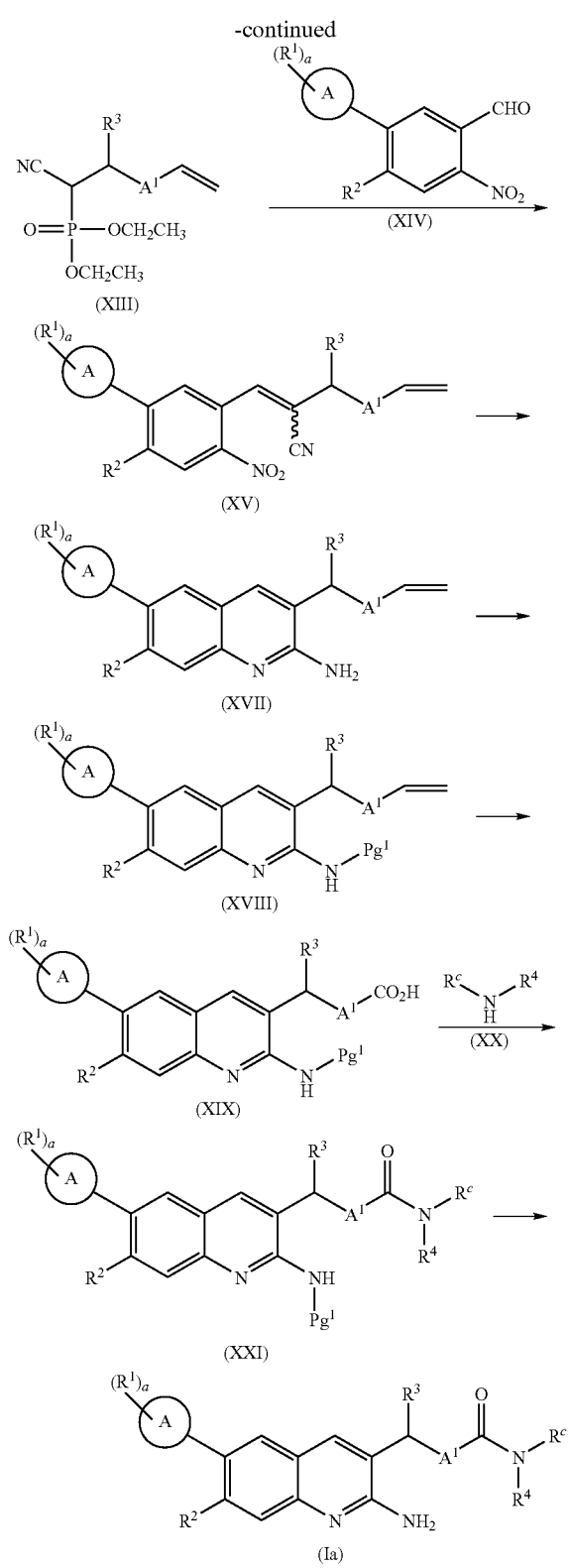

Accordingly, a suitably substituted compound of formula (X), a known compound or compound prepared by known methods is reacted with cyanomethyl-phosphonic acid diethyl ester, a known compound, in the presence of an organic amine such as NH$_4$OAc, piperidine, pyridine, and the like, in the presence of an acid such as acetic acid, formic acid, β-alanine, and the like, in an organic solvent such as toluene, ethanol, methanol, and the like, to yield the corresponding compound of formula (XI).

The compound of formula (XI) is reacted with a suitably substituted compound of formula (XII), a known compound or compound prepared by known methods, in the presence of a catalyst such as CuI, CuBr, and the like, in an organic solvent such as THF, diethyl ether, and the like, to yield the corresponding compound of formula (XIII).

The compound of formula (XIII) is reacted with a suitably substituted compound of formula (XIV), a known compound or compound prepared by known methods, in the presence of a base such as LHMDS, lithium diisopropylamide, sodium hydride, and the like, in an organic solvent such as THF, diethyl ether, and the like, at a temperature in the range of from about 60° C. to about 150° C., preferably at a temperature in the range of from about 75° C. to about 100° C., to yield a mixture of the corresponding compound of formula (XV), as a mixture of its corresponding (Z) and (E) isomers.

The compound of formula (XV) is reacted with a reducing agent such as zinc, and the like, preferably zinc, in the presence of a proton source such as ammonium chloride, calcium chloride, and the like, in an organic solvent such as methanol, ethanol, and the like, at a temperature in the range of from about 60° C. to about 150° C., preferably at a temperature in the range of from about 75° C. to about 100° C., to yield the corresponding compound of formula (XVII). Alternatively, the compound of formula (XV) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of from about 75° C. to about 100° C., to yield the corresponding compound of formula (XVII).

The compound of formula (XVII) is optionally reacted with a suitable protecting reagent, such as acetic anhydride, acetyl chloride, and the like, according to known methods, (i.e. in the presence of a base such as TEA, DMAP, and the like, in an organic solvent such as dichloromethane, chloroform, and the like) to yield the corresponding compound of formula (XVIII), wherein Pg$^1$ is the corresponding suitable nitrogen protecting group.

The compound of formula (XVIII) is reacted with an oxidizing agent such as potassium permanganate, osmium tetroxide, ruthenium tetroxide, sodium periodate, and the like, in a mixture of an organic solvent such as DCM, acetone, ethyl acetate, and the like, and water (as a co-solvent), to yield the corresponding compound of formula (XIX).

The compound of formula (XIX) is reacted with a suitably substituted compound of formula (XX), a known compound or compound prepared by known methods, in the presence of a coupling agent such as HBTU, EDCl, HOBT, and the like, in the presence of a base such as DIPEA, TEA, pyridine, and the like, in an organic solvent such as DMF, DCM, and the like, to yield the corresponding compound of formula (XXI).

The compound of formula (XXI) is de-protected according to known methods, for example by reacting with hydrazine, sodium hydroxide, and the like, in a protic solvent such as methanol or ethanol, at a temperature in the range of from about 60° C. to about 150° C., preferably at a temperature in the range of from about 75° C. to about 100° C., to yield the corresponding compound of formula (Ia).

Alternatively, compounds of formula (I) wherein L$^1$ is —C(O)—NR$^c$— may alternatively be prepared according to the process outlined in Scheme 2.

Scheme 2

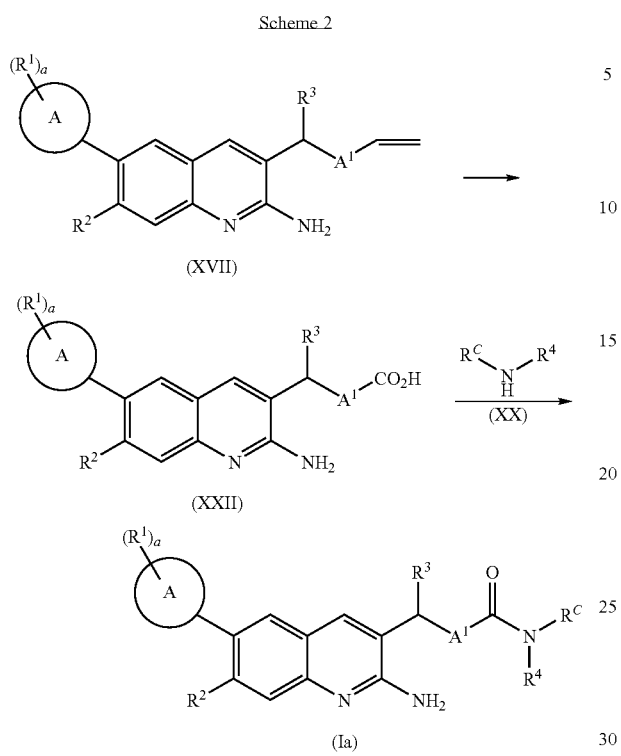

Accordingly, a compound of formula (XVII) is reacted with an oxidizing agent such as potassium permanganate, osmium tetroxide, ruthenium tetroxide, and sodium periodate and the like, in a mixture of an organic solvent such as DCM, acetone, ethyl acetate, and the like, and water (as a co-solvent), to yield the corresponding compound of formula (XXII).

The compound of formula (XXII) is reacted via a two step, one pot reaction, first with an alkyl chloroformate, such as iso-butyl chloroformate, and the like, in the presence of a base such as N-methylmorpholine, DIPEA, and the like, in an organic solvent such as dichloromethane, chloroform and the like, at a temperature less than about room temperature, preferably at a about 0° C.; and then with a suitably substituted compound of formula (XX), a known compound or compound prepared by known methods, yield the corresponding compound of formula (Ia).

Compounds of formula (I) wherein $L^1$ is $—NR^C—$ may be prepared according to the process outlined in Scheme 3, below.

Scheme 3

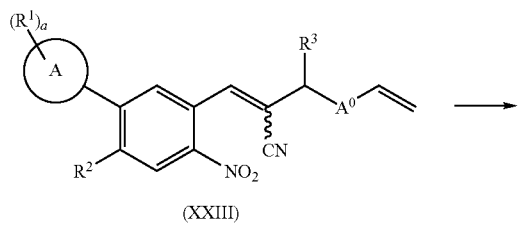

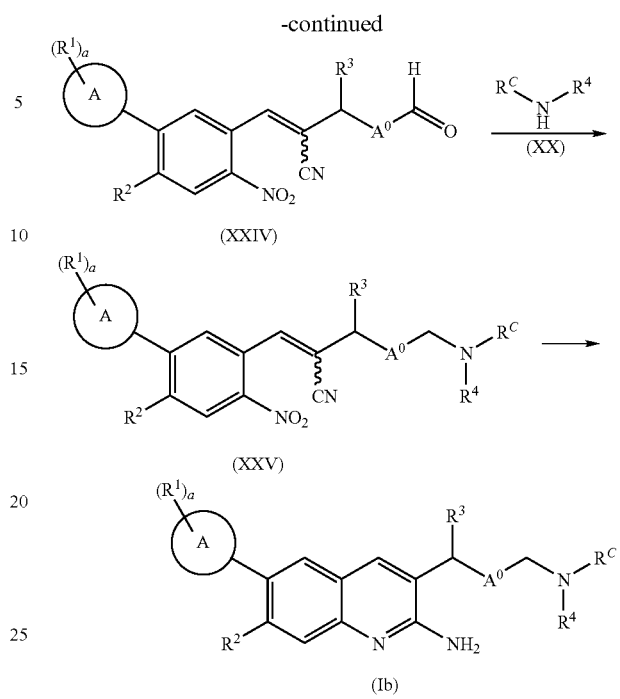

Accordingly, a suitably substituted compounds of formula (XXIII) (as a mixture of the corresponding (Z) and (E) isomers), wherein $A^0$ is $—(C_{1-3}alkyl)-$, a known compound or compound prepared by known methods, is reacted with an oxidizing agent such as potassium permanganate, osmium tetroxide, ruthenium tetroxide, sodium periodate and the like, in the presence of N-morpholineoxide, 2,6-lutidine, and the like; in a mixture of an organic solvent such as THF, t-BuOH, 1,4-dioxane, and the like, and water (as a co-solvent), to yield the corresponding compound of formula (XXIV) (as a mixture of the corresponding (Z) and (E) isomers).

The compound of formula (XXIV) is reacted with a suitably substituted compound (XX), in the presence of a reducing agent, such as sodium triacetoxyborohydride, and the like, in an organic solvent, such as dichloromethane, dichloroethane, THF, and the like, or sodium borohydride in a protic solvent such as methanol or ethanol, or the like, to yield the corresponding compound of formula (XXV) (as a mixture of the corresponding (Z) and (E) isomers). Alternatively, the compound of formula (XXIV) is reacted with a suitably substituted compound (XX), in the presence of sodium cyanoborohydride, in the presence of a catalytic amount of an acid, such as acetic acid, HCl, the like, in an organic solvent, such as methanol, acetonitrile, and the like, to yield the corresponding compound of formula (XXV).

The compound of formula (XXV) (as a mixture of corresponding (Z) and (E) isomers) is reacted with a reducing agent such as zinc, and the like, in the presence of a proton source such as ammonium chloride, calcium chloride, and the like, in an organic solvent such as methanol, ethanol, and the like, at a temperature in the range of from about 60° C. to about 150° C., preferably at a temperature in the range of form about 75° C. to about 100° C., to yield the corresponding compound of formula (Ib). Alternatively, the compound of formula (XXV) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of form about 75° C. to about 100° C., to yield the corresponding compound of formula (Ib).

Compounds of formula (I) wherein -A¹-L¹ is —(C₂₋₄ alkyl)-NRC— may alternatively be prepared from the corresponding compound of formula (Ic) wherein A⁰ is (C₁₋₃alkyl) as outlined in Scheme 4 below.

Scheme 4

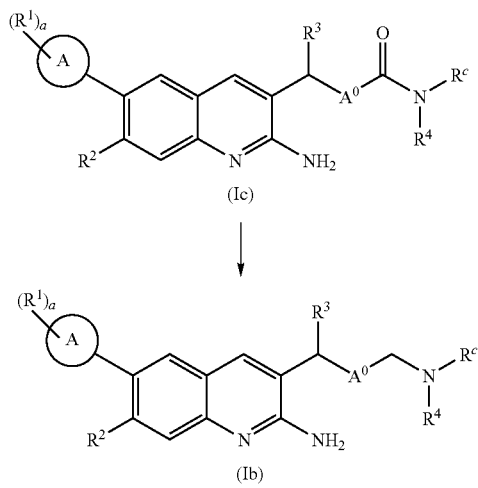

(Ic)

↓

(Ib)

Accordingly, a suitably substituted compound of formula (Ic), wherein -A⁰- is —(C₁₋₃alkyl)-is by reacting the compound of formula (Ic) with a suitably selected reducing agent such as borane-tetrahydrofuran, lithium aluminum hydride, and the like, in an organic solvent such as diethyl ether, THF, glyme, diglyme, and the like, at a temperature in the range of form about 25° C. to about 15° C., preferably at a temperature in the range of from about 50° C. to about 100° C., optionally in a microwave, to yield the corresponding compound of formula (Ib).

Compounds of formula (I) wherein L¹ is —C(O)—NR^C— may alternatively be prepared according to the process outlined in Scheme 5.

Scheme 5

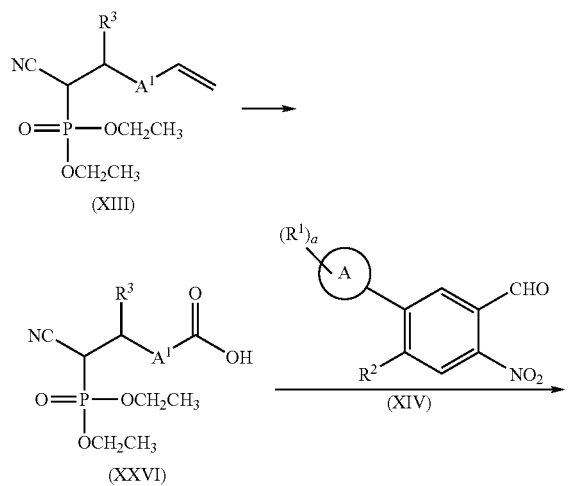

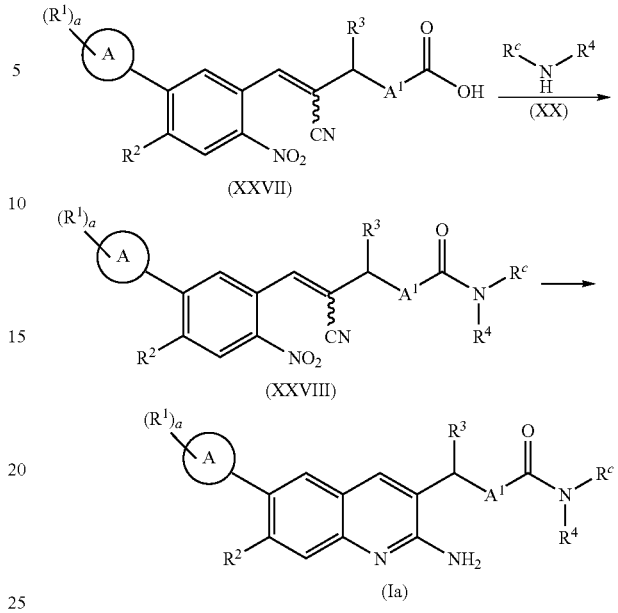

(Ia)

Accordingly, a suitably substituted compound of formula (XIII), a known compound or compound prepared by known methods, is reacted with an oxidizing agent such as potassium permanganate, osmium tetroxide or N-methylmorpholineoxide, ruthenium tetroxide, sodium periodate or periodic acid, with ruthenium oxide, ruthenium trichloride, and the like, in a mixture of an organic solvent such as DCM, acetone, ethyl acetate, and the like, and water (as a co-solvent), to yield the corresponding compound of formula (XXVI).

The compound of formula (XXVI) is reacted with a suitably substituted compound of formula (XIV), a known compound or compound prepared by known methods, in the presence of a base such as LHMDS, lithium diisopropylamide, sodium hydride, and the like, in an organic solvent such as THF, diethyl ether, and the like, at a temperature in the range of from about 60° C. to about 150° C., preferably at a temperature in the range of from about 75° C. to about 100° C., to yield a mixture of the corresponding compound of formula (XXVII), as a mixture of its corresponding (Z) and (E) isomers.

The compound of formula (XXVII) is reacted with a suitably substituted compound of formula (XX), a known compound or compound prepared by known methods, in the presence of a coupling agent such as HBTU, EDCl, HOBT, and the like, in the presence of a base such as DIPEA, TEA, pyridine, and the like, in an organic solvent such as DMF, DCM, and the like, to yield the corresponding compound of formula (XXVIII).

The compound of formula (XXVIII) is reacted with a reducing agent such as zinc, and the like, preferably zinc, in the presence of a proton source such as ammonium chloride, calcium chloride, and the like, in an organic solvent such as methanol, ethanol, and the like, at a temperature in the range of from about 60° C. to about 150° C., preferably at a temperature in the range of from about 75° C. to about 100° C., to yield the corresponding compound of formula (Ia). Alternatively, the compound of formula (XXVIII) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of from about 75° C. to about 100° C., to yield the corresponding compound of formula (Ia).

Compounds of formula (I) may alternatively be prepared according to the process outlined in Scheme 6 below.

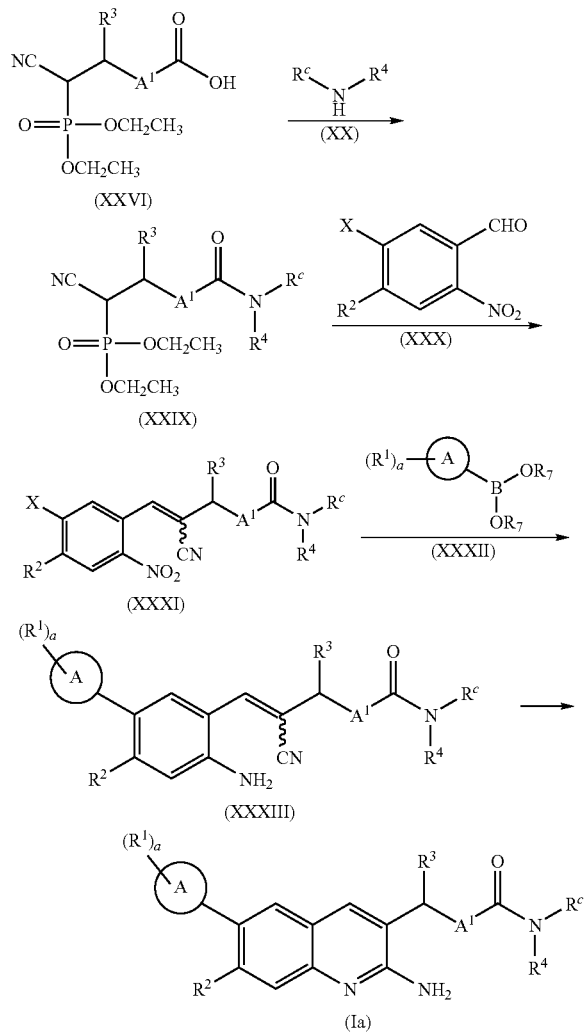

Accordingly, a suitably substituted compound of formula (XXVI), a known compound or compound prepared by known methods, is reacted with a suitably substituted compound of formula (XX), a known compound or compound prepared by known methods, in the presence of a coupling agent such as HBTU, EDCl, HOBT, and the like, in the presence of a base such as DIPEA, TEA, pyridine, and the like, in an organic solvent such as DMF, DCM, and the like, to yield the corresponding compound of formula (XXIX).

The compound of formula (XXIX) is reacted with a suitably substituted compound of formula (XXX), wherein X is bromine, iodine, or chlorine, a known compound or compound prepared by known methods, in the presence of a base such as LHMDS, lithium diisopropylamide, sodium hydride, and the like, in an organic solvent such as THF, diethyl ether, and the like, at a temperature in the range of from about 60° C. to about 150° C., preferably at a temperature in the range of from about 75° C. to about 100° C., to yield a mixture of the corresponding compound of formula (XXXI), as a mixture of its corresponding (Z) and (E) isomers.

The compound of formula (XXXI) is reacted with a suitably substituted compound of formula (XXXII), wherein the two $R^7$ groups are the same or are hydroxy or taken together to form a ring, such as 4,4,5,5-tetramethyl-1,3,2-dioxaborolane, 5,5-dimethyl-1,3,2-dioxaborinane, and the like, (i.e. the compound of formula (XXXII) is the corresponding boronic acid or cyclic borane ester), a known compound or compound prepared by known methods, in the presence of a catalyst, such as tetrakis(triphenylphosphine)palladium, dichloro(diphenylphosphinoferrocene)palladium, and the like, in the presence of a base such as potassium carbonate, sodium carbonate, and the like, in a solvent such as ethanol, toluene, and the like, in addition to water as a co-solvent, at a temperature in the range of from about 60° C. to about 150° C., preferably at a temperature in the range of from about 80° C. to about 120° C., to yield a mixture of the corresponding compound of formula (XXXIII), as a mixture of its corresponding (Z) and (E) isomers.

The compound of formula (XXXIII) is reacted with a reducing agent such as zinc, and the like, preferably zinc, in the presence of a proton source such as ammonium chloride, calcium chloride, and the like, in an organic solvent such as methanol, ethanol, and the like, at a temperature in the range of from about 60° C. to about 150° C., preferably at a temperature in the range of from about 75° C. to about 100° C., to yield the corresponding compound of formula (Ia). Alternatively, the compound of formula (XXVIII) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of from about 75° C. to about 100° C., to yield the corresponding compound of formula (Ia).

One skilled in the art will recognize that compounds of formula (I) wherein $L^1$ is selected from the group consisting of —N($R^C$)— and —C(O)—N($R^C$)— and wherein $R^C$ and $R^2$ are taken together with the nitrogen atom to which they are bound to form a ring structure as defined herein, may be similarly prepared according to the procedures described in Scheme 1, Scheme 2, Scheme 3, Scheme 5 and Scheme 6 above by selecting a suitably substituted cyclic amine for the compound of formula (XX).

Compounds of formula (I) wherein $A^1$ is —$CH_2CH_2$—, $L^1$ is —$NR^C$— and —$R^C$ and $R^4$ are taken together with the nitrogen atom to which they are bound to form 4-substituted-{1,2,3}-triazole may be prepared according to the process as outlined in Scheme 7, below.

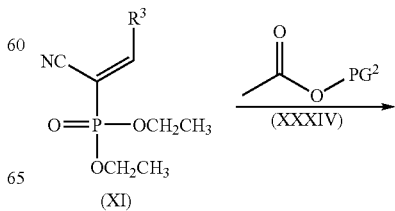

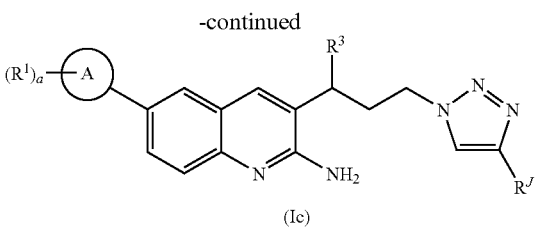

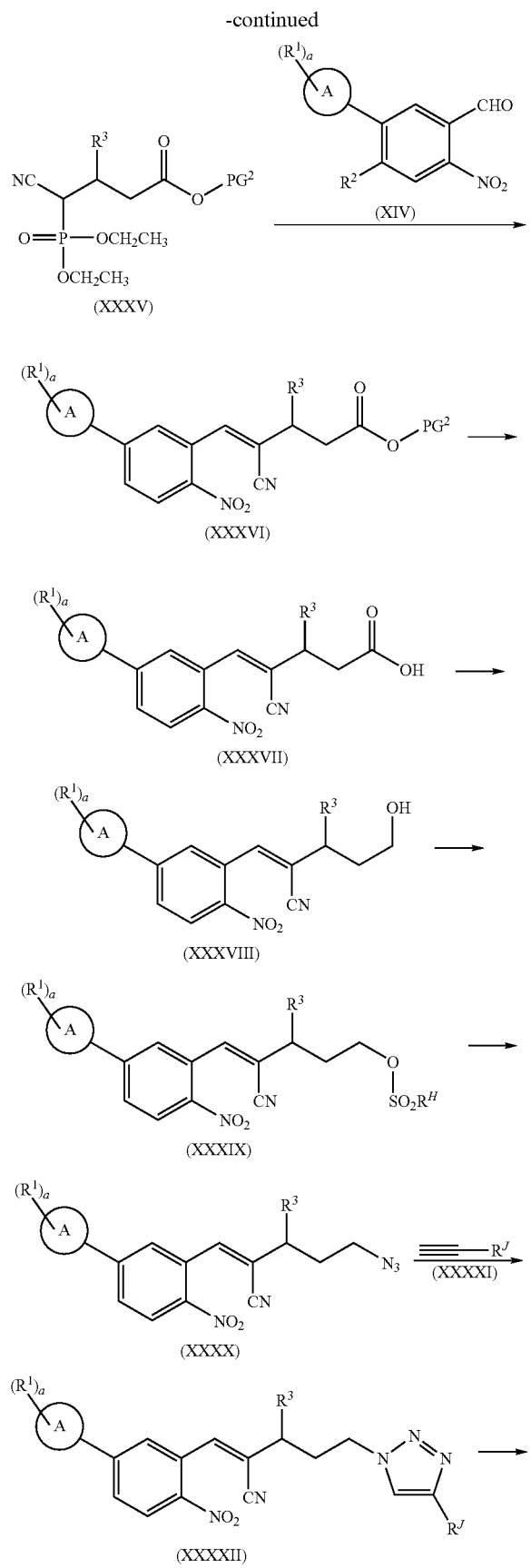

Accordingly, a suitably substituted compound of formula (XI), a known compound or compound prepared by known methods, is reacted with a suitably protected alkyl acetate, a compound of formula (XXXIV) wherein $Pg^2$ is a suitably selected protecting group such as methyl, ethyl, t-butyl, benzyl, and the like, a known compound or a compound prepared by known methods, in the presence of a base, such as LHMDS, lithium diisopropylamine, sodium hydride, and the like, in the presence of a catalyst such as CuI, CuBr, and the like, in an organic solvent such as THF, diethyl ether, and the like, to yield the corresponding compound of formula (XXXV).

The compound of formula (XXXV) is reacted with a suitably substituted compound of formula (XIV), a known compound or compound prepared by known methods, in the presence of a base, such as LHMDS, lithium diisopropylamine, sodium hydride, and the like, in an organic solvent such as THF, diethyl ether, and the like, at a temperature in the range of from about 0° C. to about 25° C., to yield the corresponding compound of formula (XXXVI).

The compound of formula (XXXVI) is de-protected according to known methods, to yield the corresponding compound of formula (XXXVII). For example, wherein $Pg^2$ is tert-butyl, the compound of formula (XXXVI) is reacted with an acid, in an organic solvent (for example with TFA in dichloromethane, or HCl in an organic solvent, such as diethyl ether, iso-propanol, ethyl acetate, and the like), to yield the corresponding compound of formula (XXXVII). Alternatively, wherein the compound of formula (XXXVI), $Pg^2$ is methyl, ethyl, and the like, the compound of formula (XXXVI) is reacted with a base such as such as lithium hydroxide, sodium hydroxide, and the like, in water or a protic solvent, such as methanol, ethanol, and the like, to yield the corresponding compound of formula (XXXVII).

The compound of formula (XXXVII) is reacted with a chloroformate, such as ethyl chloroformate, iso-butyl chloroformate, and the like, in the presence of an organic base, such as N-methylmorpholine, DIPEA, triethylamine, and the like, in an organic solvent, such as THF, tert-butylmethyl ether, and the like, at a temperature in the range of from about −20° C. to about 25° C., preferably at a temperature in the range of from about 0° C. to about 25° C. After a period of stirring, a reducing agent such as sodium borohydride, lithium borohydride, Red-Al, and the like, is added, optionally in a co-solvent, such as methanol, ethanol, and the like, to yield the corresponding compound of formula (XXXVIII).

The compound of formula (XXXVIII) is reacted with a suitably selected sulfonylating agent, for example, a compound of the formula $Cl-SO_2-R^H$, wherein $R^H$ is a suitably selected alkyl or aryl group, such that $Cl-SO_2-R^H$ is for example mesyl chloride ($Cl-SO_2-CH_3$), tosyl chloride ($Cl-SO_2$-(4-methylphenyl)), and the like, in the presence of a base such as TEA, DMAP, and the like, in an organic solvent such as dichloromethane, chloroform, and the like, at a temperature in the range of from about −20° C. to about 25° C., preferably, at a temperature in the range of from about 0° C. to about 25° C., to yield the corresponding compound of formula (XXXIX).

The compound of formula (XXXIX) is reacted with sodium azide, optionally in the presence of an iodide source, such as sodium iodide, potassium iodide, and the like, in an organic solvent such as DMF, DMSO, and the like, at a temperature in the range of from about 25° C. to about 140° C., preferably, at a temperature in the range of from about 25° C. to about 60° C., to yield the corresponding compound of formula (XXXX).

The compound of formula (XXXX) is reacted with a suitably substituted compound of formula (XXXXI), wherein $R^J$ is selected from the group consisting of $C_{1-5}$alkyl, —$C_{1-4}$alkyl-O—$C_{1-4}$alkyl, carboxy, —C(O)O—$C_{1-4}$alkyl and aralkyl, (preferably $R^J$ is selected from the group consisting of $C_{1-5}$alkyl, more preferably $R^J$ is t-butyl), a known compound or compound prepared by known methods, in the presence of a catalyst, such as copper sulfate, copper (II) acetate, and the like, in the presence of a base such as sodium ascorbate, ascorbic acid, DIPEA, and the like, in an organic solvent such as DMF, THF, methanol, ethanol, and the like, in the presence of water, to yield the corresponding compound of formula (XXXXII).

The compound of formula (XXXXII) is reacted with a suitably selected reducing agent such as zinc, and the like, in the presence of a proton source such as ammonium chloride, calcium chloride, and the like, in an organic solvent such as methanol, ethanol, and the like, at a temperature in the range of from about 60° C. to about 150° C., preferably, at a temperature in the range of from about 75° C. to about 100° C., to yield the corresponding compound of formula (Ic). Alternatively, the compound of formula (XXXXII) is reacted with a reducing agent such as stannous chloride, iron, and the like, in an acidic solvent such as aqueous HCl, acetic acid, and the like, at a temperature in the range of from about 60° C. to about 150° C., preferably at a temperature in the range of form about 75° C. to about 100° C., to yield the corresponding compound of formula (Ic).

Compounds of formula (XIV) are known compounds or compounds which may be prepared according to known methods. For example, compounds of formula (XIV) may be prepared according to the process outlined in Scheme 8, below.

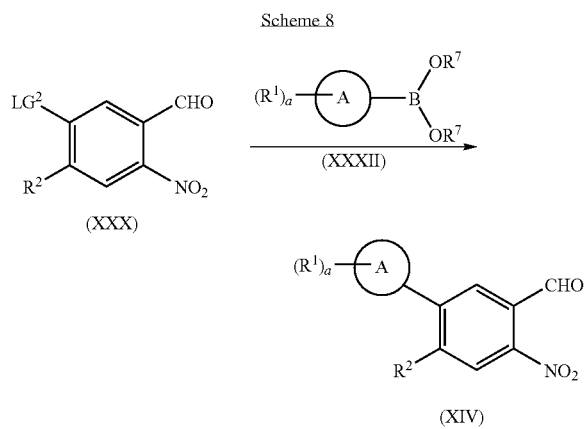

Scheme 8

Accordingly, a suitably substituted compound of formula (XXX), wherein wherein X is bromine, iodine, or chlorine, a known compound or compound prepared by known methods, is reacted with a suitably substituted, a compound of formula (XXXII), wherein the two $R^7$ groups are the same or are hydroxy or taken together in a ring, such as 4,4,5,5-tetramethyl-1,3,2-dioxaborolane, 5,5-dimethyl-1,3,2-dioxaborinane, and the like, (i.e. the compound of formula (XXXII) is the corresponding boronic acid or cyclic borane ester), a known compound or compound prepared by known methods, in the presence of a catalyst, such as tetrakis(triphenylphosphine)palladium, dichloro(diphenylphosphinoferrocene)palladium, and the like, in the presence of a base such as potassium carbonate, sodium carbonate, and the like, in a solvent such as ethanol, toluene, and the like, in addition to water as a co-solvent, at a temperature in the range of from about 60° C. to about 150° C., preferably at a temperature in the range of from about 80° C. to about 120° C., to yield a mixture of the corresponding compound of formula (XIV).

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.1-1000 mg/kg/day, preferably, at a dosage of from about 0.5 to about 500 mg/kg/day, more preferably, at a dosage of from about 0.5 to about 250 mg/kg/day, more preferably, at a dosage of from about 0.5 to about 100 mg/kg/day, more preferably, at a dosage of from about 1.0 to about 50 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg, preferably, from about 0.1 to about 500 mg, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by BACE described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, one or more of the compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of disorders mediated by BACE is required.

The daily dosage of the products may be varied over a wide range from 0.01 to 10,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.1-1,000 mg/kg/day, or any range therein, preferably, at a dosage of from about 0.5 to about 500 mg/kg/day, or any range therein, more preferably, at a dosage of from about 0.5 to about 250 mg/kg/day, or any range therein, more preferably, at a dosage of from about 0.5 to about 100 mg/kg/day, or any range therein, more preferably, at a dosage of from about 1.0 to about 50 mg/kg/day or any range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Compound #22

3-[3-(4-tert-Butyl-[1,2,3]triazol-1-yl)-1-(tetrahydro-pyran-4-yl)-propyl]-7-ethoxy-6-(2-fluoro-phenyl)-quinolin-2-ylamne

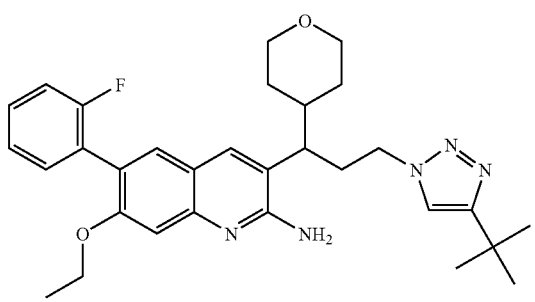

Step A: 5-Bromo-4-fluoro-2-nitro-benzaldehyde

To a solution of 3-bromo-4-fluorobenzaldehyde (5.0 g, 24.6 mmol) in $H_2SO_4$ (25 mL) at 0° C. was added nitric acid (3 mL) in $H_2SO_4$ (30 mL), dropwise. The resulting mixture was warmed to room temperature overnight. The resulting solution was then poured slowly over ice and filtered to collect the yellow precipitate. The precipitate was washed with $H_2O$ and dried, then purified by silica gel chromatography eluted with a solvent mixture of ethyl acetate and heptanes from 0:100 to 25:75 to yield a light yellow solid.

Step B: 6,2'-Difluoro-4-nitro-biphenyl-3-carbaldehyde

A solution of the yellow solid prepared as in Step A (2.0 g, 8.0 mmol), 2-fluorobenzeneboronic acid (2.3 g, 16.1 mmol) and 2M $K_2CO_3$ (12 mL) in dioxane (60 mL) was degassed with nitrogen. $Pd(PPh_3)_4$ (0.93 g, 8.0 mmol) was added, and the resulting solution was degassed again and then heated to reflux for 1 hour. The resulting mixture was then diluted with EtOAc, washed with saturated aqueous $NaHCO_3$, and brine. After drying ($MgSO_4$), the resulting mixture was filtered and concentrated in vacuo to yield a residue. Purification of the residue by silica gel chromatography eluted with a solvent mixture of ethyl acetate and heptanes from 0:100 to 5:95 yielded a light yellow solid.

Step C: 6-Ethoxy-2'-fluoro-4-nitro-biphenyl-3-carbaldehyde

A solution of NaH (456 mg, 11 mmol) in EtOH (50 mL) was stirred for 30 min. The light yellow solid prepared as in Step B (600 mg, 2.3 mmol) was added, and the resulting mixture was warmed to 30° C. After 3.5 hours at 30° C., the bath was removed, and the resulting mixture was stirred at room temperature overnight. The resulting mixture was concentrated in vacuo and adsorbed directly onto silica gel for purification. Purification by silica gel chromatography eluted with a solvent mixture of dichloromethane and heptanes from 0:100 to 50:50 yielded a yellow solid.

Step D: 1-Cyano-2-(tetrahydro-pyran-4-yl)-vinyl]-phosphonic acid diethyl ester

Tetrahydropyran carboxyaldehyde (10 g, 87.6 mmol), diethyl cyanoacetophosphonate (16.3 g, 92 mmol), acetic acid (3 mL, 50 mmol), and ammonium acetate (3 g, 38.9 mmol) were combined in toluene (60 mL) and stirred overnight at room temperature, then heated to 100° C. for two hours and then filtered through $MgSO_4$. The solvent was removed to yield an oil which was purified via silica column chromatography (50% EtOAc/heptane) to yield an oil.

Step E: 4-Cyano-5-(6-ethoxy-2'-fluoro-4-nitro-biphenyl-3-yl)-3-(tetrahydro-pyran-4-yl)-pent-4-enoic acid tert-butyl ester To a solution of tert-butyl acetate (217 μL, 1.6 mmol) in THF (0.92 mL) at −78° C., LHMDS (1.0 M in THF, 1.4 mL) was added slowly. After 30 min of stirring at −78° C., [1-cyano-2-(tetrahydro-pyran-4-yl)-vinyl]-phosphonic acid diethyl ester (302 mg, 1.1 mmol) dissolved in THF (0.92 mL) was added, followed by CuI (6.3 mg, 0.03 mmol). The resulting solution was warmed to room temperature, stirred for 2 h, and then 6-ethoxy-2'-fluoro-4-nitro-biphenyl-3-carbaldehyde (266.0 mg, 0.9195 mmol), prepared as in Step C above, was added. The resulting solution was stirred at room temperature for another 20 h. Ethyl acetate was then added, and the resulting solution was washed with hydrochloric acid solution (1.0 M) two times and with brine one time, and then dried over magnesium sulfate. The resulting solution was filtered and concentrated. The residue was purified on a silica gel column eluted with a solvent mixture of ethyl acetate and heptanes from 0:100 to 25:75 to yield a residue.

$MH^+=524.5$

Step F: 4-Cyano-5-(6-ethoxy-2'-fluoro-4-nitro-biphenyl-3-yl)-3-(tetrahydro-pyran-4-yl)-pent-4-enoic acid To a solution of the residue prepared as in Step E (163 mg, 0.3119 mmol) in dichloromethane (2.0 mL) at room temperature was added TFA (1.6 mL). The resulting solution was stirred at room temperature for 1 h and then concentrated. Diethyl ether was added and the resulting solution was extracted with sodium hydroxide solution (1M) two times. The combined aqueous extracts were acidified with conc. hydrochloric acid, and extracted with diethyl ether (3×). The organic layers were combined and dried over magnesium sulfate, filtered and concentrated to yield a residue.

$MH^+$ 468.47

Step G: 3-(6-Ethoxy-2'-fluoro-4-nitro-biphenyl-3-yl)-2-[3-hydroxy-1-(tetrahydro-pyran-4-yl)-prolyl]-acrylonitrile To a solution of the residue prepared as in Step F (111 mg, 0.237 mmol) in THF (1.2 mL) at 0° C. was added N-methylmorpholine (30.0 µL, 16.6 mmol) followed by slow addition of ethyl chloroformate (0.26 µL, 0.27 mmol). The resulting solution was stirred at 0° C. for 1 h, and then sodium borohydride (0.45 mg, 1.2 mmol) was added. Methanol (0.2 mL) was added slowly into the resulting solution, which was then stirred at room temperature for 2 h. Ethyl acetate was added. The resulting solution was washed with hydrochloric acid (1.0 M) twice and brine once and then was dried over magnesium sulfate. The resulting solution was filtered and concentrated to yield a yellow oil. The yellow oil was purified on a silica gel column eluted with a solvent mixture of ethyl acetate and heptanes from 0:100 to 35:65 to yield a yellow solid.

MH$^+$=454.49

Step H: 2-[3-Azido-1-(tetrahydro-pyran-4-yl)-propyl]-3-(6-ethoxy-2'-fluoro-4-nitro-biphenyl-3-yl)-acrylonitrile To a solution of the yellow solid prepared as in Step G and triethylamine (41 µL, 0.295 mmol) in dichloromethane (1 mL) at 0° C. was slowly added methanesulfonyl chloride (12.4 µL, 0.16 mmol). The resulting solution was stirred at 0° C. for 30 min. and then at room temperature for 30 min. The resulting solution was diluted with dichloromethane, washed with hydrochloric acid solution (1.0 M) and dried over magnesium sulfate. The resulting solution was then filtered and concentrated. The residue was dissolved in DMF (1.2 mL); sodium azide (43.5 mg, 0.67 mmol) was added and the resulting solution was stirred at 50° C. for two hours. The resulting mixture was concentrated in vacuo, loaded directly onto silica gel and purified by eluting with ethyl acetate and heptanes in a 0:100 to 25:75 ratio to yield a foamy solid.

MH$^+$ 479.50

Step I: 2-[3-(4-tert-Butyl-[1,2,3]triazol-1-yl)-1-(tetrahydro-pyran-4-yl)-propyl]-3-(6-ethoxy-2'-fluoro-4-nitro-biphenyl-3-yl)-acrylonitrile To a suspension of the foamy solid prepared as in Step H (0.056 g, 0.117 mmol) in EtOH (0.8 mL), a minimal amount of THF was added to solubolize the compound. Next, 3,3-dimethyl-1-butyne (87 µL, 0.70 mmol), sodium ascorbate (0.0046 g, 0.023 mmol), and copper (II) sulfate pentahydrate (1.5 mg, 0.006 mmol) were, followed by addition of a minimal amount of H$_2$O to maintain solubility. The resulting mixture stirred at room temperature in the dark. Additional 3,3-dimethyl-1-butyne (87 µL) was added twice more at half hour intervals, and the resulting mixture stirred overnight. Ethyl acetate was added, the resulting solution was washed with saturated sodium bicarbonate solution, water, and brine, and then was dried over magnesium sulfate to yield a residue. The residue was purified by silica gel chromatography, eluting with ethyl acetate and heptanes in a 0:100 to 35:65 ratio to yield a yellow foamy solid.

MH$^+$=561.65

Step J: 3-[3-(4-tert-Butyl-[1,2,3]triazol-1-yl)-1-(tetrahydro-pyran-4-yl)-prolyl]-7-ethoxy-6-(2-fluoro-phenyl)-quinolin-2-ylamine Into a microwave vial was combined the yellow foamy solid prepared as in Step I (0.0047 g, 0.084 mmol), Zn dust (180 mg), and solid ammonium chloride (29 mg) in MeOH. The resulting mixture was microwaved @ 95° C. for 20 minutes. The resulting solution was then filtered through Celite®, washed with MeOH and then dichloromethane and then was concentrated in vacuo to yield a residue. The residue was purified by silica gel chromatography, eluting with ethyl acetate and MeOH in a 100:0 to 90:10 ratio to yield the title compound as a white solid.

Hydrochloric acid in diethyl ether was added and the resulting solution was concentrated to yield the title compound as its corresponding HCl salt, as a light yellow solid.

MH$^+$=531.66

$^1$H NMR free base (300 MHz, MeOD): δ1.15 (s, 9H), 1.30-1.35 (m, 7H, 1.71-1.86 (m, 2H), 2.37-2.6 (m, 1H), 2.72-2.88 (m, 1H), 3.31-3.41 (m, 2H), 3.82-3.87 (m, 1H), 3.95-3.97 (m, 1H), 4.14 (q, J=6.78 Hz, 2H), 4.24-4.36 (m, 2H), 7.04 (s, 1H), 7.10-7.25 (m, 2H), 7.34-7.41 (m, 2H), 7.53 (s, 2H), 7.89 (s, 1H)

Example 2

Compound #47

4-[2-Amino-6-(2-fluoro-phenyl)-quinolin-3-yl]-N-(3,3-dimethyl-butyl)-N-(2-morpholin-4-yl-ethyl)-4-(tetrahydro-pyran-4-yl)-butyramide

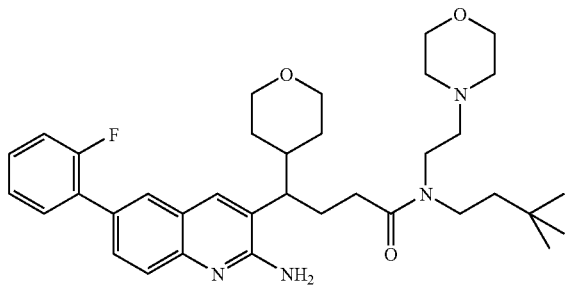

Step A: [1-Cyano-2-(tetrahydro-pyran-4-yl)-hex-5-enyl]-phosphonic acid diethyl ester In a flask, Mg (5.7 g) was placed in THF (50 mL) with an iodine chip. The reaction mixture was vigorously stirred and heated slightly, as 4-bromobutene (25 mL) was added. After consumption of Mg metal, the resulting solution was cannulated into a flask containing a mixture of [1-cyano-2-(tetrahydro-pyran-4-yl)-vinyl]-phosphonic acid diethyl ester (21.78 g, 79.7 mmol), prepared as described in Example 1 Step D above, and CuI (0.3 g) with THF (30 mL). The resulting mixture was stirred for three hours. Saturated aqueous NH$_4$Cl solution and ethyl acetate were then added. The organic layer was separated and dried with MgSO$_4$, filtered, and evaporated in vacuo to yield an oil.

Step B: 5-Cyano-5-(diethoxy-phosphoryl)-4-(tetrahydro-pyran-4-yl)-pentanoic acid To a solution of [1-cyano-2-(tetrahydro-pyran-4-yl)-hex-5-enyl]-phosphonic acid diethyl ester (6.26 g, 19.0 mmol) in dichloromethane (211 mL), H$_2$O (173 mL) and acetic acid (73 mL), was added tetrabutylammonium bromide (127 mg) followed by the portionwise addition of KMnO$_4$. The resulting mixture was then stirred at room temperature overnight. The resulting viscous solution was cooled to 0° C., and NaHSO$_3$ was added slowly until the mixture became clear. The layers were separated, and the organic layer was dried over magnesium sulfate, filtered, and concentrated to yield a residue. Heptanes was added, and the resulting mixture was concentrated to yield a residue.

MH+ 347.35

Step C: 5-Bromo-2-nitro-benzaldehyde

Sulfuric acid (108 mL) and 3-bromobenzaldehyde (25 g, 0.135 mol) were cooled to 0° C. in a flask. Potassium nitrate (14.3 g, 0.14 mol) was added to the resulting mixture, portion wise over 1 h. The resulting mixture was stirred an additional 2 h at 0° C. For work up, the resulting mixture was poured into 2 L of ice and then filtered to yield a solid. The solid was purified by silica chromatography (330 g, 30% $Et_2O$/heptane) to yield a residue, which was recrystallized from EtOAc/heptane to yield a solid.

Step D: 2'-Fluoro-4-nitro-biphenyl-3-carbaldehyde

A solution of 5-bromo-2-nitrobenzaldehyde (8.2 g, 36 mmol), 2-fluorobenzeneboronic acid (10.0 g, 71.6 mmol) and 2M $K_2CO_3$ (54 mL) in dioxane (250 mL) was degassed with nitrogen. $Pd(PPh_3)_4$ (3.9 g, 3.6 mmol) was added, and the resulting mixture was degassed again and heated to reflux for 90 minutes. The resulting mixture was then diluted with EtOAc and washed with saturated aqueous $NaHCO_3$ solution and brine. The EtOAc extract was dried with $MgSO_4$, filtered, and concentrated in vacuo to yield a residue. The residue was purified by silica gel chromatography eluted with ethyl acetate and heptanes from 0:100 to 5:95 to yield a yellow solid.

$^1$H NMR (300 MHz, $CDCl_3$): δ7.19-7.33 (m, 2H), 7.4-7.53 (m, 2H), 7.94 (dt, J=8.29, 1.88 Hz, 1H), 8.11 (s, 1H), 8.22 (d, J=8.67 Hz, 1H), 10.50 (s, 1H)

Step E: 5-Cyano-6-(2'-fluoro-4-nitro-biphenyl-3-yl)-4-(tetrahydro-pyran-4-yl)-hex-5-enoic acid To a solution of the residue prepared as in Step B (6.7 g, 19.2 mmol) in THF (385 mL) at −78° C. was slowly added LHMDS (1.0 M in THF, 41 mL). After 30 min of stirring at −78° C., the resulting mixture was warmed to room temperature, and the yellow solid prepared as in Step D (4.7 g, 19.2 mmol) was added. The resulting solution was stirred at room temperature for another 20 h. Ethyl acetate was then added, and the resulting solution was washed with hydrochloric acid solution (1.0 M) and with brine, then dried over magnesium sulfate. The resulting solution was filtered and concentrated to yield a residue. The residue was purified on a silica gel column eluted with a solvent mixture of dichloromethane and MeOH (95:5) to yield a brown solid.

$MH^+$=438.45

Step F: (3,3-Dimethyl-butyl)-(2-morpholin-4-yl-ethyl)-amine

Into a microwave reactor was placed 4-(2-chloroethyl)-morpholine (1.5 g, 8.1 mmol), 3,3-dimethylbutylamine (2.2 mL, 16 mmol), diisopropylethylamine (3.1 mL, 18 mmol), and acetonitrile (30 mL). The resulting mixture was microwaved at 130° C. for 30 minutes and then diluted with dichloromethane and 1N sodium hydroxide. The layers were separated, and the organic extract was washed with brine, dried over magnesium sulfate, filtered, and concentrated to yield an orange oil. The oil was purified on a silica gel column, eluting with 15% of 10:1 ($MeOH:NH_4OH$) in EtOAc to yield a yellow oil.

$^1$H NMR (300 MHz, $CDCl_3$) δ0.87-0.94 (m, 9H), 1.35-1.46 (m, 2H), 2.42-2.51 (m, 8H), 2.58-2.66 (m, 1H), 2.72 (t, J=6.03 Hz, 1H), 3.67-3.74 (m, 4H)

Step G: 5-Cyano-6-(2'-fluoro-4-nitro-biphenyl-3-yl)-4-(tetrahydro-pyran-4-yl)-hex-5-enoic acid (3,3-dimethyl-butyl)-(2-morpholin-4-yl-ethyl)-amide To a solution of the solid prepared as in Step E (3.2 g, 7.3 mmol) in DMF (30 mL), were added the yellow oil prepared as in Step F (1.7 g, 8.0 mmol), HBTU (4.1 g, 10.9 mmol), and DIEA (3.8 mL, 21.8 mmol). The resulting mixture was stirred 24 hours at room temperature, then diluted with EtOAc. The resulting solution was washed with saturated aqueous $NaHCO_3$ and brine several times, then dried over magnesium sulfate and concentrated to a foamy solid. The foamy solid was purified on silica gel eluting with a solvent mixture of dichloromethane and MeOH from 100:0 to 96:4 to yield a brown solid.

$MH^+$ 634.78.

Step H: 4-[2-Amino-6-(2-fluoro-phenyl)-quinolin-3-yl]-N-(3,3-dimethyl-butyl)-N-(2-morpholin-4-yl-ethyl)-4-(tetrahydro-pyran-4-yl)-butyramide A mixture of the brown solid (2.25 g, 3.7 mmol) prepared as in Step G above, zinc powder (25 g), ammonium chloride (7.8 g), MeOH (90 mL), and THF (17 mL) was heated at reflux. After three hours, the resulting mixture was cooled to room temperature, filtered through Celite®, and washed with MeOH/dichloromethane. The filtrate was concentrated to yield a solid which was purified on a silica gel column, eluting with 10% of 10:1 ($MeOH:NH_4OH$) in EtOAc to yield the title compound as a yellow solid.

The HCl salt of the title compound was prepared by dissolving the yellow solid (506 mg) in a small amount of ethanol and then concentrating with 1M HCl/diethyl ether (3×) to yield a white solid.

LCMS $MH^+$ 604.80

$^1$H NMR (HCl salt) (300 MHz, MeOD) δ 1.31 (d, J=7.54 Hz, 2H), 1.39-1.54 (m, 3H), 1.99 (s, 3H), 2.28-2.44 (m, 3H), 2.96 (s, 1H), 3.14-3.28 (m, 4H), 3.37 (d, J=3.01 Hz, 1H), 3.46 (s, 1H), 3.58-3.72 (m, 4H), 3.78-3.93 (m, 3H), 3.99-4.11 (m, 3H), 7.25-7.37 (m, 2H), 7.43-7.52 (m, 1H), 7.60 (td, J=7.72, 1.88 Hz, 1H), 7.80 (d, J=8.67 Hz, 1H), 7.99-8.05 (m, 1H), 8.16 (s, 1H), 8.54 (s, 1H)

Example 3

Compound #43

3-[4-[(3,3-Dimethyl-butyl)-(2-morpholin-4-yl-ethyl)-amino]-1-(tetrahydro-pyran-4-yl)-butyl]-6-(2-fluoro-phenyl)-quinolin-2-ylamine

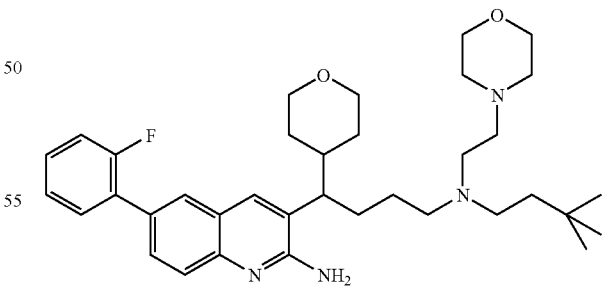

To the white solid (1.13 g, 1.9 mmol) prepared as in Example 2, Step H, above in THF (190 mL) was added $BH_3$.THF (1M in THF, 28 mL). The resulting mixture was degassed with nitrogen and then heated at reflux. After 2.5 hours, the resulting mixture was cooled to room temperature, and HCl was added slowly until a pH<5 was obtained. The resulting mixture was again heated to reflux for 30 minutes, then cooled to room temperature, concentrated in vacuo to yield a residue. The residue was adsorbed directly onto silica gel in MeOH and purified eluting with 10% of 10:1 (MeOH: NH$_4$OH) in EtOAc to give yield a second residue. The second residue was purified by Gilson HPLC (gradient elution of 20:80 CH$_3$CN/H$_2$O/0.1% TFA to 75:25 CH$_3$CN/H$_2$O/0.1% TFA) to yield the title compound as its corresponding TFA salt. The concentrated product was dissolved in a small amount of EtOH and then concentrated with 1N HCl/diethyl ether (3×), then concentrated with diethyl ether (2×) in EtOH to yield the title compound as a white solid, as its corresponding HCl salt.

LCMS MH$^+$ 590.81

$^1$H NMR (300 MHz, MeOD): δ0.88 (s, 9H), 1.19 (t, J=7.16 Hz, 2H), 1.35-2.0 (m, 9H), 2.96-3.54 (m, 13H), 3.37-3.68 (m, 4H), 3.62 (q, J=7.03 Hz, 4H), 3.90-4.06 (m, 4H), 7.25-7.38 (m, 2H), 7.44-7.52 (m, 1H), 7.61 (td, J=7.82, 1.70 Hz, 1H), 7.79 (d, J=8.67 Hz, 1H), 8.02 (d, J=8.67 Hz, 1H), 8.19 (s, 1H), 8.57 (s, 1H)

Example 4

Compound #31

4-(2-Amino-6-thiophen-2-yl-quinolin-3-yl)-N-(3,3-dimethyl-butyl)-N-(1-methyl-1H-imidazol-2-ylmethyl)-4-(tetrahydro-pyran-4-yl)-butyraide

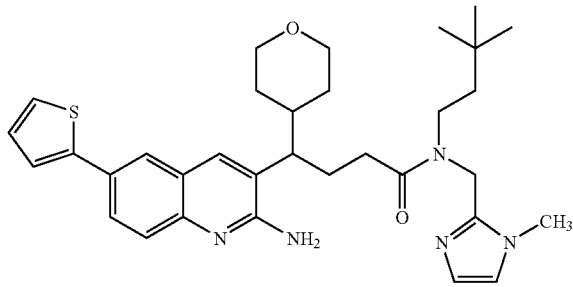

Step A: (3,3-Dimethyl-butyl)-(1-methyl-1H-imidazol-2-ylmethyl)-amine

A solution of 1-methyl-2-imidazolecarboxaldehyde (4 g, 0.036 mol) and 3,3-dimethylbutylamine (4.9 mL, 0.036 mol) in MeOH (100 mL) was stirred at room temperature for 1 hour before NaBH$_4$ (2.0 g, 0.053 mol) was added in portions. The resulting solution was stirred at room temperature for another hour before quenching with water. MeOH was removed under vacuum from the resulting mixture, and the residue purified by column chromatography (0-15% MeOH/EtOAc) to yield a light yellow liquid.

MH$^+$ 196.2

Step B: [1-Cyano-4-[(3,3-dimethyl-butyl)-(1-methyl-1H-imidazol-2-ylmethyl)-carbamoyl]-2-(tetrahydro-pyran-4-yl)-butyl]-phosphonic acid diethyl ester To an ice cooled solution of the light yellow liquid prepared as in Step A above (1.8 g, 9 mmol), 5-cyano-5-(diethoxyphosphoryl)-4-(tetrahydro-pyran-4-yl)-pentanoic acid (3.0 g, 8.7 mmol, prepared as described in Example 2, Step B) and HOBT (1.5 g, 11 mmol) in CH$_2$Cl$_2$ (100 mL), was added TEA (2.4 mL) followed by the addition of 1,3-dimethylamino propyl-3-ethylcarbodiimide (EDC, 2.2 g, 11 mmol). The resulting mixture was allowed to warm to room temperature and then stirred overnight. EtOAc (200 mL) was added. The resulting solution was washed with dilute HCl solution (about 0.1N, 50 mL), saturated aqueous NaHCO$_3$ solution, and then brine. The organic layer was dried with MgSO$_4$, and the EtOAc was evaporated to yield an oil.

MH$^+$ 525.5

Step C: 6-(5-Bromo-2-nitro-phenyl)-5-cyano-4-(tetrahydro-pyran-4-yl)-hex-5-enoic acid (3,3-dimethyl-butyl)-(1-methyl-1H-imidazol-2-ylmethyl)-amide To an ice cooled solution of the oil prepared as in Step B above (2.2 g, 4.2 mmol) in THF (10 mL), was added LHMDS (1.0M in THF, 5.0 mL) and the resulting solution was stirred for 10 min. 5-Bromo-2-nitro-benzaldehyde (1.0 g, 4.2 mmol, synthesized as described in Example 2, Step C) in THF (10 mLI) was added, the resulting solution was allowed to warm to room temperature and then stirred overnight. The reaction was quenched with aqueous NH$_4$Cl solution, and the resulting solution was extracted with EtOAc. The organic layer was dried with MgSO$_4$. The EtOAc was evaporated to yield an oil.

MH$^+$ 600.2, 602.3

Step D: 6-(5-Bromo-2-nitro-phenyl)-5-cyano-4-(tetrahydro-pyran-4-yl)-hex-5-enoic acid (3,3-dimethyl-butyl)-(1-methyl-1H-imidazol-2-ylmethyl)-amide A solution of the oil prepared as in Step C (0.2 g, 0.33 mmol), 3-thiopheneboronic acid (0.045 g, 0.34 mmol), tetrakis (triphenylphosphine) palladium (0) (0.02 g), and K$_2$CO$_3$ (0.092 g) in toluene/EtOH/water (5/2/1 mL) was refluxed one hour. EtOAc (100 mL) was added, and the resulting solution was washed with saturated aqueous NaCl solution. The organic layer was dried with MgSO$_4$, and the EtOAc was evaporated to yield an oil.

MH$^+$ 605

Step E: 4-(2-Amino-6-thiophen-2-yl-quinolin-3-yl)-N-(3,3-dimethyl-butyl)-N-(1-methyl-1H-imidazol-2-ylmethyl)-4-(tetrahydro-pyran-4-yl)-butyramide A mixture of the oil prepared as in Step E above (0.2 g, 0.33 mmol), Zn dust (0.3 g) and NH$_4$Cl (0.06 g) in MeOH (5 mL) was subjected to microwave at 130° C. for 5 min. The resulting solid was filtered out, and the filtrate was concentrated under vacuum to yield an oil. The oil was purified by Gilson HPLC to yield the title compound as a white solid, as its corresponding TFA salt.

MH$^+$ 574.3

$^1$H NMR (300 MHz, MeOD) δ 0.73 (s, 9H), 1.17-1.55 (m, 6H), 1.90-2.07 (m, 4H), 2.27-2.45 (m, 3H), 2.92 (br s, 1H), 3.36 (d, J=3.01 Hz, 1H), 3.46 (t, J=11.11 Hz, 1H), 3.86 (s, 3H), 3.91 (br s, 1H), 4.03 (dd, J=11.87, 3.58 Hz, 1H), 4.61-4.81 (m, 2H), 7.44 (d, J=1.88 Hz, 1H), 7.49 (d, J=1.88 Hz, 1H), 7.60 (d, J=1.88 Hz, 2H), 7.78 (d, J=8.67 Hz, 1H), 7.83 (t, J=2.26 Hz, 1H), 8.10-8.23 (m, 2H), 8.45 (s, 1H).

Example 5

Compound #51

4-[2-Amino-6-(2-ethoxy-phenyl)-quinolin-3-yl]-N-(3,3-dimethyl-butyl)-N-(1-methyl-1H-imidazol-2-ylmethyl)-4-(tetrahydro-pyran-4-yl)-butyramide

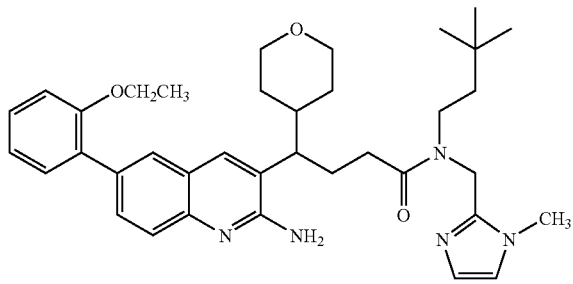

Step A: 5-Cyano-6-(2'-ethoxy-4-nitro-biphenyl-3-yl)-4-(tetrahydro-pyran-4-yl)-hex-5-enoic acid (3,3-dimethyl-butyl)-(1-methyl-1H-imidazol-2-ylmethyl)-amide A solution of the oil prepared as in Example 4, Step C above (0.17 g, 0.28 mmol), 2-ethoxybenzylboronic acid (0.063 g, 0.3 mmol), tetrakis(triphenyl-phosphine) palladium (0) (0.02 g) and $K_2CO_3$ (0.08 g) in toluene/EtOH/water (3/3/1 mL) was refluxed overnight. EtOAc (100 mL) was added, then the resulting solution was washed with saturated aqueous NaCl solution. The organic layer was dried over $MgSO_4$, and the EtOAc was evaporated to yield an oil.

$MH^+$ 642.5

Step B: 4-[2-Amino-6-(2-ethoxy-phenyl)-quinolin-3-yl]-N-(3,3-dimethyl-butyl)-N-(1-methyl-1H-imidazol-2-ylmethyl)-4-(tetrahydro-pyran-4-yl)-butyramide A mixture of the oil prepared as in Step A above (0.13 g, 0.2 mmol), Zn dust (0.2 g) and $NH_4Cl$ (0.06 g) in MeOH (5 mL) was subjected to microwave at 130° C. for 5 min. The resulting solid was filtered out and the filtrate was concentrated under vacuum to yield an oil. The oil was purified by Gilson HPLC to yield the title compound as an off-white solid, as its corresponding TFA salt.

$MH^+$ 612.5

$^1$H NMR (300 MHz, MeOD) δ 0.62 (s, 9H), 1.15 (d, J=3.39 Hz, 3H), 1.22 (t, J=6.97 Hz, 3H), 1.27-1.47 (m, 3H), 1.75-1.97 (m, 4H), 2.26 (s, 4H), 2.81 (br s, 1H), 3.28 (br s, 1H), 3.74 (s, 3H), 3.79 (br s, 1H), 3.87-3.95 (m, 1H), 3.99 (q, J=7.03 Hz, 2H), 4.55-4.67 (m, 2H), 6.91-7.05 (m, 2H), 7.26 (d, J=7.54 Hz, 2H), 7.33 (d, J=1.88 Hz, 1H), 7.38 (d, J=1.88 Hz, 1H), 7.62 (d, J=8.67 Hz, 1H), 7.88-7.96 (m, 2H), 8.35 (s, 1H)

Example 6 in vitro BACE Assay-1

This assay was run by CEREP (Catalog Ref. 761-B, Referred to SOP No. 1C131; ERMOLIEFF, J., LOY, J. A., KOELSCH, G. and TANG, J., Proteolytic activation of recombinant pro-memapsin 2 (pro-BACE) studied with new fluorogenic substrates, Biochemistry, (2000) Vol. 39, p. 12450).

More specifically the assay, run at 50 µL in a 96 well plate, evaluated the effect of test compound on the activity of the human BACE-1 quantified by measuring the formation of Mca-S-E-V-N-L-$NH_2$ from Mca-S-E-V-N-L-D-A-E-F-R-K(Dnp)-R—R—$NH_2$, using a recombinant enzyme.

The test compound, reference compound or water (control) was added to a buffer containing 0.09 M sodium acetate (pH 4.5) and 0.25 µg BACE-1. Compound interference with the fluorimetric detection method due to autofluorescence was then checked by measurements at the wavelengths defined to evaluate the enzyme activity. Thereafter, the reaction was initiated by adding 7.5 µM of the substrate Mca-S-E-V-N-L-D-A-E-F-R-K(Dnp)-R—R—$NH_2$ and the mixture was incubated for 60 min at 37° C. For control basal measurement, the substrate was omitted from the reaction mixture. Immediately after the incubation, the fluorescence intensity emitted by the reaction product Mca-S-E-V-N-L-$NH_2$ was measured at λex=320 nm and λem=405 nm using a microplate reader (Ultra, Tecan). The standard inhibitory reference compound was OM99-2, which was tested in each experiment at several concentrations to obtain an inhibition curve from which its $IC_{50}$ value was calculated.

Representative compounds of the present invention were tested in the assay as described above, with results as listed in Table 3, below.

TABLE 3

| | % Inhibition and $IC_{50}$ | | |
|---|---|---|---|
| ID No | $IC_{50}$ (µM) | % Inh @ 1 µM | % Inh @ 10 µM |
| 1 | | | 34 |
| 2 | | | 59 |
| 3 | | | 35 |
| 4 | | | 71 |
| 5 | | | |
| 6 | >5.00 | | 43 |
| 7 | 0.26 | | 83 |
| 8 | | | |
| 9 | | | 126 |
| 10 | 0.83 | | 47 |
| 11 | | 28 | |
| 12 | 0.35 | | 74.5 |
| 13 | | | 77 |
| 14 | | | |
| 15 | 0.54 | | 113 |
| 16 | >0.62 | | 88 |
| 17 | 1.40 | | 73 |
| 18 | | | 77 |
| 19 | | | 14 |
| 20 | 0.89 | | 92 |
| 21 | 0.69 | 87 | |
| 22 | 0.15 | | 65 |
| 23 | 0.57 | 97 | |
| 24 | 1.40 | | 93 |
| 25 | 0.32 | | 72 |
| 26 | | | |
| 27 | 1.8 | | 91 |
| 28 | 0.88 | | 74 |
| 29 | 1.50 | 54 | |
| 30 | | | |
| 31 | 0.42 | 79 | 98 |
| 33 | | | |
| 34 | 0.39 | | 68 |
| 35 | 0.33 | | 116 |
| 36 | 0.50 | 76 | |
| 37 | | | 82 |
| 38 | 0.47 | | 69 |
| 39 | 0.35 | 93 | |
| 41 | 0.45 | | 65 |
| 42 | 0.32 | | 65 |
| 43 | | | 78 |
| 45 | 0.53 | 94 | |
| 46 | 0.36 | | 70 |
| 47 | 0.37 | | 58 |
| 49 | | | 99 |
| 50 | | | 22 |

TABLE 3-continued

% Inhibition and IC$_{50}$

| ID No | IC$_{50}$ (μM) | % Inh @ 1 μM | % Inh @ 10 μM |
|---|---|---|---|
| 51 | 0.32 | | 99 |
| 52 | 3.60 | | 55 |
| 53 | 2.20 | | 55 |
| 54 | | | 8 |
| 55 | 2.40 | | 90 |
| 56 | | | 73 |

Example 7

In Vivo Testing

Compounds of the present invention may be further tested for their effectiveness in the treatment of disorders mediated by the BACE enzyme, for example Alzheimer's disease, by testing the compounds in an in vivo assay, for example, as disclosed in Sirinathsinghji, D. J. S. (Merck Sharp and Dohme Research Laboratories, Neuroscience Research Centre, Essex, UK.),*Transgenic mouse models of Alzheimer's disease*, Biochemical Society Transactions (1998), 26(3), pp 504-508;

Van Leuven, F. (Experimental Genetics Group, Center for Human Genetics, Flemish Institute for Biotechnology (VIB), K. U. Leuven, Louvain, Belg.), *Single and multiple transgenic mice as models for Alzheimer's disease*, Progress in Neurobiology (Oxford) (2000), 61(3), pp 305-312;

Hsiao, K.; Chapman, P.; Nilsen, S.; Eckman, C.; Harigaya, Y.; Younkin, S.; Yang, F.; Cole, G. (Dep. Neurology, Univ. Minnesota, Minneapolis, Minn., USA), *Correlative memory deficits, Aβ elevation, and amyloid plaques in transgenic mice*, Science (Washington, D.C.) (1996), 274(5284), pp 99-102 (Tg2576 mice);

Oddo, S.; Caccamo, A.; Shepherd, J. D.; Murphy, M. P.; Golde, T. E.; Kayed, R.; Metherate, R.; Mattson, M. P.; Akbari, Y.; LaFerla, F. M. (Department of Neurobiology and Behavior, University of California, Irvine, Irvine, Calif., USA), *Triple-transgenic model of Alzheimer's disease with plaques and tangles: Intracellular Aβ and synaptic dysfunction*, Neuron (2003), 39(3), pp 409-421 (APP Triple Transgenic Mice);

Ruberti, F.; Capsoni, S.; Comparini, A.; Di Daniel, E.; Franzot, J.; Gonfloni, S.; Rossi, G.; Berardi, N.; Cattaneo, A. (Neuroscience Program, International School for Advanced Studies (SISSA), Trieste, Italy), *Phenotypic knockout of nerve growth factor in adult transgenic mice reveals severe deficits in basal forebrain cholinergic neurons, cell death in the spleen, and skeletal muscle dystrophy*, Journal of Neuroscience (2000), 20(7), pp 2589-2601 (AD11 mice);

Games, D.; Adams, D.; Alessandrini, R.; Barbour, R.; Berthelette, P.; Blackwell, C.; Carr, T.; Clemens, J.; Donaldson, T.; et al. (Athena Neurosciences, Inc., South San Francisco, Calif., USA), *Alzheimer-type neuropathology in transgenic mice overexpressing V717F β-amyloid precursor protein*, Nature (London) (1995), 373(6514), pp 523-7 (V717F mice);

Neve, R. L.; Boyce, F. M.; McPhie, D. L.; Greenan, J.; Oster-Granite, M. L. (Dep. Genetics, Harvard Medical School and McLean Hospital, Belmont, Mass., USA), *Transgenic mice expressing APP-C100 in the brain*, Neurobiology of Aging (1996), 17(2), pp191-203 (APP-C100 mice);

and/or as disclosed in U.S. Pat. No. 5,811,633; U.S. Pat. No. 5,877,399; U.S. Pat. No. 5,672,805; U.S. Pat. No. 5,720,936; U.S. Pat. No. 5,612,486; U.S. Pat. No. 5,580,003; U.S. Pat. No. 5,850,003; U.S. Pat. No. 5,387,742; U.S. Pat. No. 5,877,015; U.S. Pat. No. 5,811,633; U.S. Pat. No. 6,037,521; U.S. Pat. No. 6,184,435; U.S. Pat. No. 6,187,922; U.S. Pat. No. 6,211,428; and U.S. Pat. No. 6,340,783.

Example 8

Human Testing

Compounds of the present invention may be further tested for their effectiveness in the treatment of disorders mediated by the BACE enzyme, for example Alzheimer's disease, by testing the compounds in human subjects, for example, as disclosed in Lins, H.; Wichart, I.; Bancher, C.; Wallesch, C.-W.; Jellinger, K. A.; Roesler, N. (Department of Neurology, Otto-von-Guericke-University, Magdeburg, Germany), *Immunoreactivities of amyloid β peptide(1-42) and total τ protein in lumbar cerebrospinal fluid of patients with normal pressure Hydrocephalus*, Journal of Neural Transmission (2004), 111(3), pp 273-280;

Lewczuk, P.; Esselmann, H.; Otto, M.; Maler, J. M.; Henkel, A. W.; Henkel, M. K.; Eikenberg, O.; Antz, C.; Krause, W.-R.; Reulbach, U.; Kornhuber, J.; Wiltfang, J. (Department of Psychiatry and Psychotherapy, Molecular Neurobiology Lab, University of Erlangen-Nuremberg, Erlangen, Germany), *Neurochemical diagnosis of Alzheimer's dementia by CSF Aβ42, Aβ42/Aβ40 ratio and total tau*, Neurobiology of Aging (2004), 25(3), pp 273-281;

Olsson, A.; Hoglund, K.; Sjogren, M.; Andreasen, N.; Minthon, L.; Lannfelt, L.; Buerger, K.; Moller, H.-J.; Hampel, H.; Davidsson, P.; Blennow, K. (Sahlgrenska University Hospital, Experimental Neuroscience Section, Institute of Clinical Neuroscience, Goteborg University, Moelndal, Sweden), *Measurement of α- and β-secretase cleaved amyloid precursor protein in cerebrospinal fluid from Alzheimer patients*, Experimental Neurology (2003), 183(1), pp 74-80;

Wahlund, L.-O.; Blennow, K. (Karolinska Institute, Section of Geriatric Medicine, Department of Clinical Neuroscience and Family Medicine, Huddinge University Hospital, Stockholm, Sweden), *Cerebrospinal fluid biomarkers for disease stage and intensity in cognitively impaired patients*, Neuroscience Letters (2003), 339(2), pp 99-102;

El Mouedden, M., Vandermeeren, M., Meert, T., Mercken, M. (Johnson & Johnson Pharmaceutical Research and Development, Division of Janssen Pharmaceutica N.V., Turnhoutseweg 30, Beerse, Belg.), *Development of a specific ELISA for the quantitative study of amino-terminally truncated beta-amyloid peptides*, Journal of Neuroscience Methods (2005), 145(1-2), pp 97-105;

Vanderstichele, H., Van Kerschaver, E., Hesse, C., Davidsson, P., Buyse, M.-A., Andreasen, N., Minthon, L., Wallin, A., Blennow, K., Vanmechelen, E., (Innogenetics NV, Ghent, Belg.), *Standardization of measurement of β-amyloid(1-42) in cerebrospinal fluid and plasma*, Amyloid (2000), 7(4), pp 245-258;

and/or Schoonenboom, N. S., Mulder, C., Van Kamp, G. J., Mehta, S. P., Scheltens, P., Blankenstein, M. A., Mehta, P. D., *Amyloid β38, 40, and 42 species in cerebrospinal fluid: More of the same?*, Annals of Neurology (2005), 58(1), pp 139-142.

Example 9

Prophetic Example

As a specific embodiment of an oral composition, 100 mg of the compound prepared as in Example 2 or 3 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

$$\text{(I)}$$

(R$^1$)$_a$—(A)—[quinoline core with R$^2$, R$^3$, N, NH$_2$, and side chain CH(R$^3$)-A$^1$-L$^1$-R$^4$]

wherein a is an integer from 0 to 4;

R$^1$ is selected from the group consisting of halogen, C$_{1-4}$alkyl, C$_{1-4}$alkoxy, halogenated C$_{1-4}$alkyl and halogenated C$_{1-4}$alkoxy;

(A) is selected from the group consisting of aryl and heteroaryl;

R$^2$ is selected from the group consisting of hydrogen and C$_{1-4}$alkoxy;

R$^3$ is selected from the group consisting of hydrogen, C$_{1-8}$alkyl, hydroxy substituted C$_{2-8}$alkyl, NR$^A$R$^B$ substituted C$_{2-8}$alkyl, —C$_{1-4}$alkyl-O—C$_{1-4}$alkyl, cycloalkyl, —(C$_{1-4}$alkyl)-cycloalkyl, heterocycloalkyl and —(C$_{1-4}$alkyl)-heterocycloalkyl; wherein R$^A$ and R$^B$ are each independently selected from the group consisting of hydrogen and C$_{1-4}$alkyl;

A$^1$ is selected from the group consisting of —(CH$_2$)$_b$—; wherein b is an integer from 2 to 4;

L$^1$ is selected from the group consisting of —NR$^C$— and —C(O)—NR$^C$—; wherein R$^C$ is selected from the group consisting of hydrogen, C$_{1-8}$alkyl, hydroxy substituted C$_{1-4}$alkyl, —C$_{1-4}$alkyl-O—C$_{1-4}$alkyl and C$_{5-7}$cycloalkyl;

R$^4$ is selected from the group consisting of C$_{1-8}$alkyl, C$_{2-12}$alkenyl, —C$_{1-4}$alkyl-O—C$_{1-4}$alkyl, —C$_{1-4}$alkyl-NR$^D$R$^E$, —C$_{1-4}$alkyl-OH, cycloalkyl, —C$_{1-4}$alkyl-cycloalkyl, partially unsaturated carbocyclyl, —C$_{1-4}$alkyl-(partially unsaturated carbocyclyl), aryl, aralkyl, heteroaryl, —C$_{1-4}$alkyl-heteroaryl, heterocycloalkyl and —C$_{1-4}$alkyl-heterocycloalkyl;

wherein R$^D$ and R$^E$ are each independently selected from the group consisting of hydrogen and C$_{1-4}$alkyl;

and wherein the cycloalkyl, partially unsaturated carbocyclyl, aryl, heteroaryl or heterocycloalkyl, whether alone or as part of a substituent group, is optionally substituted with one or more substituents independently selected from the group consisting of fluoro, C$_{1-4}$alkyl, —C$_{1-4}$alkyl-O—C$_{1-4}$alkyl, carboxy, —C(O)O—C$_{1-4}$alkyl and aralkyl;

alternatively, L$^1$ is —NR$^C$— and R$^C$ and R$^4$ are taken together with the nitrogen atom to which they are attached to form a ring structure selected from the group consisting of 1-pyrazolyl, 1-imidazolyl and 1-(1,2,3-triazolyl); wherein the 1-pyrazolyl, 1-imidazolyl or 1-(1,2,3-triazolyl) is optionally substituted with a substituent selected from the group consisting of C$_{1-6}$alkyl;

or a pharmaceutically acceptable salt thereof.

2. A compound as in claim 1, wherein a is an integer from 0 to 3;

R$^1$ is selected from the group consisting of halogen, C$_{1-4}$alkoxy, halogenated C$_{1-4}$alkyl and halogenated C$_{1-4}$alkoxy;

(A) is selected from the group consisting of aryl and heteroaryl;

R$^2$ is selected from the group consisting of hydrogen and C$_{1-4}$alkoxy;

R$^3$ is selected from the group consisting of C$_{1-8}$alkyl, hydroxy substituted C$_{2-8}$alkyl, NR$^A$R$^B$ substituted C$_{2-8}$alkyl, cycloalkyl, —(C$_{1-4}$alkyl)-cycloalkyl, heterocycloalkyl and —(C$_{1-4}$alkyl)-heterocycloalkyl; wherein R$^A$ and R$^B$ are each independently selected from the group consisting of hydrogen and C$_{1-4}$alkyl;

A$^1$ is selected from the group consisting of —(CH$_2$)$_b$—; wherein b is an integer from 2 to 4;

L$^1$ is selected from the group consisting of —NR$^C$— and —C(O)—NR$^C$—; wherein R$^C$ is selected from the group consisting of hydrogen, C$_{1-8}$alkyl, hydroxy substituted C$_{1-4}$alkyl and C$_{5-7}$cycloalkyl;

R$^4$ is selected from the group consisting of C$_{1-8}$alkyl, —C$_{1-4}$ alkyl-O—C$_{1-4}$alkyl, —C$_{1-4}$alkyl-NR$^D$R$^E$, —C$_{1-4}$ alkyl-OH, cycloalkyl, —C$_{1-4}$alkyl-cycloalkyl, aryl, aralkyl, heteroaryl, —C$_{1-4}$alkyl-heteroaryl, heterocycloalkyl and —C$_{1-4}$alkyl-heterocycloalkyl;

wherein R$^D$ and R$^E$ are each independently selected from the group consisting of hydrogen and C$_{1-4}$alkyl;

and wherein the cycloalkyl, partially unsaturated carbocyclyl, aryl, heteroaryl or heterocycloalkyl, whether alone or as part of a substituent group, is optionally substituted with one or more substituents independently selected from the group consisting of fluoro, C$_{1-4}$alkyl, carboxy, —C(O)O—C$_{1-4}$alkyl and aralkyl;

alternatively, L$^1$ is —NR$^C$— and R$^C$ and R$^4$ are taken together with the nitrogen atom to which they are attached to form a ring structure selected from the group consisting of 1-pyrazolyl, 1-imidazolyl and 1-(1,2,3-triazolyl); wherein the 1-pyrazolyl, 1-imidazolyl or 1-(1,2,3-triazolyl) is optionally substituted with a substituent selected from the group consisting of C$_{1-6}$alkyl;

or a pharmaceutically acceptable salt thereof.

3. A compound as in claim 2, wherein a is an integer from 0 to 2;

R$^1$ is selected from the group consisting of halogen, C$_{1-2}$alkoxy, fluorinated C$_{1-2}$alkyl and fluorinated C$_{1-2}$alkoxy;

(A) is selected from the group consisting of aryl and heteroaryl;

R$^2$ is selected from the group consisting of hydrogen and C$_{1-2}$alkoxy;

R³ is selected from the group consisting of cycloalkyl and heterocycloalkyl;
A¹ is selected from the group consisting of —(CH₂)_b—; wherein b is an integer from 2 to 3;
L¹ is selected from the group consisting of —NR^C— and —C(O)—NR^C—; wherein R^C is selected from the group consisting of hydrogen, C_{1-8}alkyl and cycloalkyl;
R⁴ is selected from the group consisting of C_{1-8}alkyl, hydroxy substituted C_{1-6}alkyl, —C_{1-4}alkyl-O—C_{1-4}alkyl-, cycloalkyl, —C_{1-2}alkyl-cycloalkyl, aralkyl, heteroaryl, —C_{1-2}alkyl-heteroaryl and —C_{1-2}alkyl-heterocycloalkyl; wherein the cycloalkyl, aryl, heteroaryl or heterocycloalkyl, whether alone or as part of a substituted group is optionally substituted with C_{1-4}alkyl;
alternatively, L¹ is —NR^C— and R^C and R⁴ are taken together with the nitrogen atom to which they are bound to form 1-(1,2,3-triazolyl); wherein the 1,2,3-triazolyl is optionally substituted with a C_{1-4}alkyl;
or a pharmaceutically acceptable salt thereof.

4. A compound as in claim 3, wherein
a is an integer from 0 to 2;
R¹ is selected from the group consisting of fluoro, methoxy, ethoxy, trifluoromethyl and trifluoromethoxy;

is selected from the group consisting of phenyl, 2-thienyl, 2-pyrrolyl, 2-pyridyl and 7-indolyl;
R² is selected from the group consisting of hydrogen, methoxy and ethoxy;
R³ is selected from the group consisting of (S)-cyclohexyl and 4-tetrahydropyranyl;
A¹ is selected from the group consisting of —CH₂CH₂— and —CH₂CH₂CH₂—;
L¹ is selected from the group consisting of —NR^C— and —C(O)—NR^C—; wherein R^C is selected from the group consisting of hydrogen, methyl, 3,3-dimethyl-n-butyl and cyclohexyl;
R⁴ is selected from the group consisting of 1-(3,3,-dimethyl-n-butyl), 1-hydroxy-ethyl-, 1-(2,2-dimethyl-3-hydroxy-n-propyl), t-butoxy-ethyl, cyclohexyl, 1-adamantyl, cyclopropyl-methyl-, cyclohexyl-methyl-, benzyl, 2-(1-methyl-imidazolyl), 2-pyridyl-methyl-, 1-pyrrolidinyl-ethyl-, 5-thiazolyl-methyl- and 4-morpholinyl-ethyl-;
alternatively, L¹ is —NR^C— and R^C and R⁴ are taken together with the nitrogen atom to which they are bound to form 1-(4-t-butyl-1,2,3-triazolyl);
or a pharmaceutically acceptable salt thereof.

5. A compound as in claim 4, wherein
a is an integer from 1 to 2;
R¹ is selected from the group consisting of fluoro, methoxy and ethoxy;

is selected from the group consisting of phenyl and 2-thienyl;
R² is selected from the group consisting of hydrogen, methoxy and ethoxy;
R³ is 4-tetrahydropyranyl;
A¹ is selected from the group consisting of —CH₂CH₂— and —CH₂CH₂CH₂—;
L¹ is selected from the group consisting of —NR^C— and —C(O)—NR^C—; wherein R^C is selected from the group consisting of hydrogen, 3,3-dimethyl-n-butyl and cyclohexyl;
R⁴ is selected from the group consisting of 1-(3,3-dimethyl-n-butyl), t-butoxy-ethyl, 1-adamantyl, cyclohexyl-methyl-, benzyl, 2-(1-methyl-imidazolyl), 2-pyridyl-methyl-, 1-pyrrolidinyl-ethyl-, 5-thiazolyl-methyl- and 4-morpholinyl-ethyl-;
alternatively, L¹ is —NR^C— and R^C and R⁴ are taken together with the nitrogen atom to which they are bound to form 1-(4-t-butyl-1,2,3-triazolyl);
or a pharmaceutically acceptable salt thereof.

6. A compound as in claim 4, wherein
a is an integer from 1 to 2;
R¹ is selected from the group consisting of fluoro and ethoxy;

is selected from the group consisting of phenyl and 2-thienyl;
R² is hydrogen;
R³ is 4-tetrahydropyranyl;
A¹ is —CH₂CH₂—;
L¹ is —C(O)—NR^C—; wherein R^C is selected from the group consisting of hydrogen, 3,3-dimethyl-n-butyl and cyclohexyl;
R⁴ is selected from the group consisting of 1-(3,3-dimethyl-n-butyl), cyclohexyl-methyl-, benzyl, 2-(1-methyl-imidazolyl), 2-pyridyl-methyl-, 1-pyrrolidinyl-ethyl-, 5-thiazolyl-methyl- and 4-morpholinyl-ethyl-;
or a pharmaceutically acceptable salt thereof.

7. A compound as in claim 4, wherein
a is 1;
R¹ is selected from the group consisting of fluoro, methoxy and trifluoromethoxy;

is selected from the group consisting of phenyl, 2-thienyl and 7-indolyl;
R² is selected from the group consisting of hydrogen and ethoxy;
R³ is 4-tetrahydropyranyl;
A¹ is selected from the group consisting of —CH₂CH₂— and —CH₂CH₂CH₂—;
L¹ is selected from the group consisting of —NR^C— and —C(O)—NR^C—; wherein R^C is selected from the group consisting of hydrogen, methyl and 3,3-dimethyl-n-butyl;
R⁴ is selected from the group consisting of 1-(3,3,-dimethyl-n-butyl), 1-adamantyl, cyclohexyl-methyl-, 2-(1-methyl-imidazolyl), 5-thiazolyl-methyl- and 4-morpholinyl-ethyl-;
alternatively, L¹ is —NR^C— and R^C and R⁴ are taken together with the nitrogen atom to which they are bound to form 1-(4-t-butyl-1,2,3-triazolyl);
or a pharmaceutically acceptable salt thereof.

8. A compound as in claim 4, wherein a is 1;

$R^1$ is selected from the group consisting of fluoro, methoxy and trifluoromethoxy;

(A)

is selected from the group consisting of phenyl and 7-indolyl;

$R^2$ is hydrogen;

$R^3$ is 4-tetrahydropyranyl;

$A^1$ is selected from the group consisting of —CH$_2$CH$_2$— and —CH$_2$CH$_2$CH$_2$—;

$L^1$ is selected from the group consisting of —NR$^C$— and —C(O)—NR$^C$—; wherein R$^C$ is selected from the group consisting of hydrogen, methyl and 3,3-dimethyl-n-butyl;

$R^4$ is selected from the group consisting of 1-(3,3,-dimethyl-n-butyl), 1-adamantyl, cyclohexyl-methyl-, 2-(1-methyl-imidazolyl), 5-thiazolyl-methyl- and 4-morpholinyl-ethyl-;

or a pharmaceutically acceptable salt thereof.

9. A pharmaceutical composition comprising a pharmaceutically acceptable carrier and a compound of claim 1.

10. A pharmaceutical composition made by mixing a compound of claim 1 and a pharmaceutically acceptable carrier.

11. A process for making a pharmaceutical composition comprising mixing a compound of claim 1 and a pharmaceutically acceptable carrier.

* * * * *